United States Patent
Lin et al.

(10) Patent No.: US 10,117,837 B2
(45) Date of Patent: Nov. 6, 2018

(54) METHODS OF PREPARING STIMULI-RESPONSIVE MULTIFUNCTIONAL NANOPARTICLES

(71) Applicant: National Tsing Hua University, Hsinchu (TW)

(72) Inventors: Chun-Jui Lin, Hsinchu (TW); Tzu-Wei Wang, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 15/446,387

(22) Filed: Mar. 1, 2017

(65) Prior Publication Data
US 2018/0250237 A1    Sep. 6, 2018

(51) Int. Cl.
| | |
|---|---|
| *A61K 38/00* | (2006.01) |
| *A61K 9/50* | (2006.01) |
| *A61K 49/00* | (2006.01) |
| *A61K 47/48* | (2006.01) |
| *A61K 38/09* | (2006.01) |

(52) U.S. Cl.
CPC ........... *A61K 9/5036* (2013.01); *A61K 38/09* (2013.01); *A61K 47/4823* (2013.01); *A61K 49/0091* (2013.01)

(58) Field of Classification Search
CPC .. A61K 9/5036; A61K 38/09; A61K 47/4823; A61K 49/0091
See application file for complete search history.

(56) References Cited

U.S. PATENT DOCUMENTS

2010/0129439 A1* 5/2010 Alexis ............... A61K 39/00
424/451

OTHER PUBLICATIONS

Chun-Jui Lin et at., "Integrated self-assembling drug delivery system possessing dual responsive and active targeting for orthotopic ovarian cancer theranostics", Biomaterials 90, (2016),pp. 12-26, Taiwan.

* cited by examiner

*Primary Examiner* — Aradhana Sasan
*Assistant Examiner* — Quanglong N Truong
(74) *Attorney, Agent, or Firm* — WPAT, PC

(57) ABSTRACT

Provided is a method of preparing a stimuli-responsive multifunctional nanoparticle, including in sequence the steps of: (a) conjugating covalently an active targeting moiety to a hydrophilic polymer to form a targeted polymer, (b) conjugating covalently a redox-responsive moiety to the hydrophilic polymer of the targeted polymer to form a targeted redox-responsive polymer, (c) conjugating covalently a pH-responsive moiety of a drug complex to the redox-responsive moiety of the targeted redox-responsive polymer to form a targeted stimuli-responsive polymer-drug conjugate, wherein the drug complex includes a hydrophobic drug covalently linked to the pH-responsive moiety, and (d) adding the targeted stimuli-responsive polymer-drug conjugate and optionally an imaging agent into an aqueous liquid to allow self-assembly into a stimuli-responsive multifunctional nanoparticle, wherein the hydrophobic drug of the stimuli-responsive multifunctional nanoparticle forms a hydrophobic core, and the imaging agent is incorporated within the hydrophobic core.

11 Claims, 21 Drawing Sheets

Specification includes a Sequence Listing.

SEQUENCE LISTING

```
<160> NUMBER OF SEQ ID NOS: 1

<210> SEQ ID NO 1
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (10)..(10)
<223> OTHER INFORMATION: AMIDATION

<400> SEQUENCE: 1

Glu His Trp Ser Tyr Gly Leu Arg Pro Gly
1               5                   10
```

METHODS OF PREPARING STIMULI-RESPONSIVE MULTIFUNCTIONAL NANOPARTICLES

BACKGROUND OF THE INVENTION

1. Field of the Invention

The present invention relates to methods of preparing nanoparticles. Particularly, the present invention relates to methods of preparing stimuli-responsive multifunctional nanoparticles for delivery of both drug and imaging agents.

2. The Prior Art

In recent years, research in nanotechnology has been largely focusing on development of nanoparticles as a platform for delivery of drug or imaging agents in the body in order to treat or diagnose diseases, especially for delivery of anticancer drugs. The goals of nanoparticle development include increase of safety and biocompatibility, drug delivery with high specificity, high drug loading efficiency, extension of the circulating half-life, and controlled and complete drug release. By stable drug encapsulation in nanoparticles during blood circulation and complete drug release from the collapsed nanoparticles in target cells, the effective concentrations of drugs acting on target cells would be elevated and the toxic side effects to normal tissues would be reduced. However, it is difficult for the currently known nanoparticles to possess all the advantages mentioned above because of the designs and the preparation procedures.

For example, liposomes, which are composed of lipids, have become the dominant carriers of anticancer drugs in the current market due to their good biocompatibility and biodegradability. Nevertheless, they possess poor structural stability in the blood. Drug leakage from liposomes before arrival at the pathological site causes side effects, including nausea, vomiting, loss of appetite, and hair loss. Though it has been reported that surface modifications of nanoparticles with polyethylene glycol (PEG) may decrease their clearance from blood by the mononuclear phagocytic system, elongate their circulation half-time in blood, and improve their stability, lower uptake of liposomes with PEG modification by cells has been observed. Even if the PEG-modified liposomes are taken up by target cells, a lack of mechanisms for accelerated drug release from liposomes leads to incomplete release of drugs and thus the lowered effective concentration.

Therefore, it is of great necessity to develop novel preparation methods to obtain newly designed nanoparticles with all features including high specificity, prolonged circulation time, controlled and complete drug release, and multifunctionality.

SUMMARY OF THE INVENTION

As a result, the present invention provides a method of preparing a stimuli-responsive multifunctional nanoparticle, including in sequence the steps of: (a) conjugating covalently an active targeting moiety to a hydrophilic polymer to form a targeted polymer, (b) conjugating covalently a redox-responsive moiety to the hydrophilic polymer of the targeted polymer to form a targeted redox-responsive polymer, (c) conjugating covalently a pH-responsive moiety of a drug complex to the redox-responsive moiety of the targeted redox-responsive polymer to form a targeted stimuli-responsive polymer-drug conjugate, wherein the drug complex includes a hydrophobic drug covalently linked to the pH-responsive moiety, and (d) adding the targeted stimuli-responsive polymer-drug conjugate into an aqueous liquid to allow self-assembly into a stimuli-responsive multifunctional nanoparticle, wherein the hydrophobic drug of the stimuli-responsive multifunctional nanoparticle forms a hydrophobic core. The method of the present invention further includes the step of adding an imaging agent into the aqueous liquid in step (d) to allow the imaging agent to be incorporated within the hydrophobic core of the stimuli-responsive multifunctional nanoparticle.

In one embodiment of the present invention, the imaging agent is a near-infrared fluorescent dye such as cyanine 5.5, and the hydrophilic polymer and the active targeting moiety in step (a) are specific for cancer cells.

In another embodiment of the present invention, the hydrophilic polymer in step (a) is hyaluronic acid with a molecular weight of below 20 kDa, preferably hyaluronic acid with a molecular weight of about 16 kDa; the active targeting moiety in step (a) is a peptide with 5-20 amino acid residues, preferably a peptide with about 10 amino acid residues, such as a luteinizing hormone-releasing hormone peptide (also termed LHRH peptide) or an analog thereof; the redox-responsive moiety in step (b) includes a redox-responsive linkage such as a disulfide bond, and it may be cystamine or an analog thereof; the pH-responsive moiety in step (c) includes an acid-labile linkage that is hydrolyzed below pH 7, and it may be a cis-aconityl group; the hydrophobic drug in step (c) may be an anticancer drug.

In still another embodiment of the present invention, the targeted stimuli-responsive polymer-drug conjugate and the imaging agent in step (d) are in a weight ratio of about 10:1 to 15:1.

In yet another embodiment of the present invention, the stimuli-responsive multifunctional nanoparticle is at a size of about 150-300 nm, which allows penetration of the nanoparticle across fenestrated vascular walls (with openings of about a hundred to several hundred nanometers) into tumors.

The stimuli-responsive multifunctional nanoparticle of the present invention is of low toxicity to normal or non-target cells and is safe to use because it is made of materials that are biodegradable.

Moreover, the stimuli-responsive multifunctional nanoparticle promotes endocytosis by target cancer cells other than normal cells due to the presence of the cancer-targeting hydrophilic polymers, such as hyaluronic acid, and the active targeting moieties that are specifically recognized by cancer cells, such as the LHRH peptide. This enhanced specificity prevents cytotoxicity and unwanted side effects to normal tissues. The stimuli-responsive multifunctional nanoparticle has also been demonstrated to achieve prolonged circulation time under physiological conditions and controlled and complete drug release in target cells through the stimuli-responsive covalent linkages that are stable outside the target cells but are cleaved upon environmental changes in pH and redox potential inside the target cells.

Furthermore, the stimuli-responsive multifunctional nanoparticle is applicable to both cancer treatment and diagnosis, because it may carry both the therapeutic anticancer drugs and the imaging agents. This combination delivery allows tracking of the tumors using the non-invasive in vivo imaging system (IVIS) and adjusting prescription medication doses based on the latest diagnostic information.

The present invention is further explained in the following drawings and examples. It is understood that the examples given below do not, however, limit the scope of the invention, and it will be evident to those skilled in the art that modifications can be made without departing from the scope of the appended claims.

DETAILED DESCRIPTION OF THE PREFERRED EMBODIMENT

The present invention provides a method of preparing a stimuli-responsive multifunctional nanoparticle, comprising in sequence the steps of: (a) conjugating covalently an active targeting moiety to a hydrophilic polymer to form a targeted polymer, (b) conjugating covalently a redox-responsive moiety to the hydrophilic polymer of the targeted polymer to form a targeted redox-responsive polymer, (c) conjugating covalently a pH-responsive moiety of a drug complex to the redox-responsive moiety of the targeted redox-responsive polymer to form a targeted stimuli-responsive polymer-drug conjugate, wherein the drug complex includes a hydrophobic drug covalently linked to the pH-responsive moiety, and (d) adding the targeted stimuli-responsive polymer-drug conjugate into an aqueous liquid to allow self-assembly into a stimuli-responsive multifunctional nanoparticle, wherein the hydrophobic drug of the stimuli-responsive multifunctional nanoparticle forms a hydrophobic core. The method may further includes the step of adding an imaging agent into the aqueous liquid in step (d) to allow the imaging agent to be incorporated within the hydrophobic core of the stimuli-responsive multifunctional nanoparticle.

Figure 1:
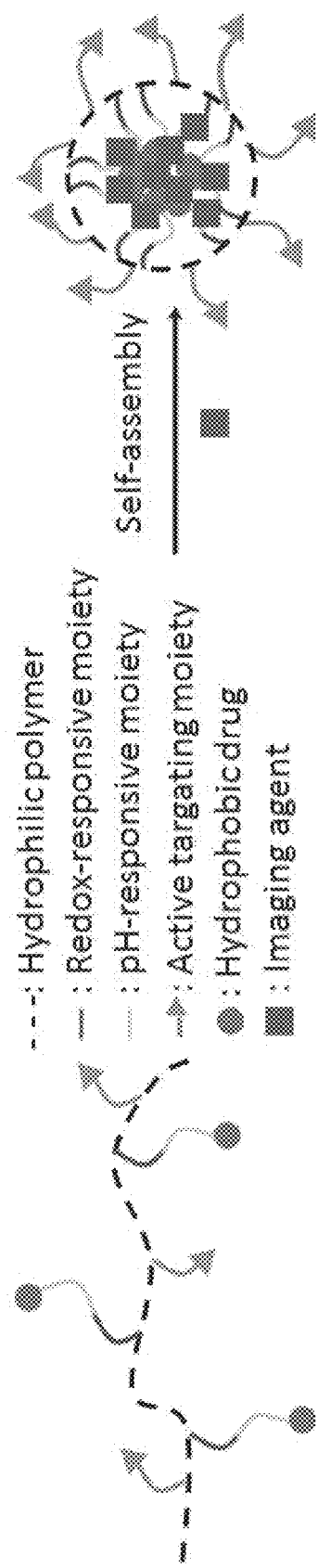
FIG. 1 is a pictorial description of formation of the stimuli-responsive multifunctional nanoparticle of the present invention by self-assembly of the targeted stimuli-responsive polymer-drug conjugate and spontaneous incorporation of imaging agents.

FIG. 1 illustrates formation of the stimuli-responsive multifunctional nanoparticle of the present invention by self-assembly of the targeted stimuli-responsive polymer-drug conjugate and spontaneous incorporation of imaging agents.

The stimuli-responsive multifunctional nanoparticle prepared according to the method has been demonstrated to release drug in response to acidic pH and a reductive environment, which marked the endosomal (pH 4-6) and cytosolic (10-20 mM glutathione) conditions inside of target cells. In one embodiment, the stimuli-responsive multifunctional nanoparticle exhibited significantly more cytotoxicity to ovarian cancer cells, suggesting specific cellular uptake by cancer cells other than normal cells. When monitored by in vivo imaging system, the stimuli-responsive multifunctional nanoparticle accumulated in the ovarian tumor of an orthotopic ovarian tumor xenograft model. Therefore, the stimuli-responsive multifunctional nanoparticle of the present invention is applicable to cancer therapy and diagnostics as it possesses high specificity to target cancer cells and exhibits stimuli-responsive controlled and complete release of hydrophobic drugs and imaging agents.

Definition

Numerical quantities given herein are approximate, and experimental values may vary within 20 percent, preferably within 10 percent, and most preferably within 5 percent. Thus, the terms "about" and "approximately" refer to within 20 percent, preferably within 10 percent, and most preferably within 5 percent of a given value or range.

As used herein, the terms "hydrophobic drug" includes hydrophobic drugs for treatment of diseases such as cancers. These drugs include anticancer drugs used in chemotherapy, for example, doxorubicin, paclitaxel, and cisplatin, antimetastatic drugs or agents, for example, matrix metalloproteinase (MMP) inhibitors, angiogenesis inhibitors, and latrunculin B, and substances for gene therapy.

As used herein, the term "imaging agents" includes substances that are able to be detected and monitored by imaging systems and are used for diagnosis of diseases such as cancers. These agents include organic materials, inorganic materials, and organic-inorganic hybrid materials, for example, iron oxide, fluorophore, quantum dot, and carbon dot.

As used herein, the term "analog" refers to a chemical or a biomaterial such as a peptide that has a structure or a sequence similar to that of the indicated chemical or biomaterial.

Materials and Methods

Materials

Hyaluronic acid (HA) was purchased from LIFECORE Biomedical Co. Ltd. (U.S.A.). 1-Ethyl-3-(3-dimethylaminopropyl) carbodiimide (EDC), N-Hydroxy-succinimide (NHS), doxorubicin hydrochloride (DOX.HCl) and ethyl acetate were purchased from Sigma-Aldrich Co. Ltd. (U.S.A). Cystamine dihydrochloride, sodium metaperiodate ($NaIO_4$) and cis-aconitic anhydride were purchased from Alfa Aeser Co. Ltd. (UK). Chloroform was purchased from JTBaker Co. Ltd. (U.S.A.). 1,4-dioxane was purchased from Acros Organics Co. Ltd. (Belgium). Dimethylformamide was purchased from Merck Co. Ltd. (Germany) Luteinizing hormone-releasing hormone peptide, also termed LHRH peptide, was purchased from ProSpec Co. Ltd. (Israel). Dulbecco's Modified Eagle Medium (DMEM), fetal bovine serum (FBS) and Penicillin Streptomycin mixtures were purchased from Life Technology Co. Ltd. (U.S.A.).

Cell Culture

Human ovarian cancer cell line OVCAR-3 (BCRC 60551; derived from ATCC HTB-161) and mouse embryonic fibroblast cell line NIH3T3 (BCRC 60008; derived from ATCC CRLa-1658) were purchased from Bioresource Collection and Research Center, Food Industry Research and Development Institute (Hsinchu, Taiwan). OVCAR-3 cells stably expressing a firefly luciferase gene (OVCAR-3/luc cells) were prepared by transfection of the OVCAR-3 cells with an expression vector containing a luciferase gene using general molecular biology techniques. All the cells mentioned above were cultured in DMEM (high glucose) containing 10% (v/v) FBS and 1% (v/v) Penicillin Streptomycin mixtures. Cell culture was maintained at 37° C. and 5% $CO_2$ in a humidified incubator.

Establishment of an Orthotopic Ovarian Cancer Xenograft Model

The orthotopic human ovarian cancer xenograft model was established using 6-8 week old female athymic nude mice purchased from National Laboratory Animal Center (Taipei, Taiwan). All mouse procedures were approved by the Institutional Animal Care and Use Committee (IACUC) of National Tsing Hua University. Prior to surgery, the mouse was laid dorsal side up under anesthetic. The incision was made left or right of the midline and directly above the ovarian fat pad. The ovarian fat pad was gently pulled out and rested onto a sterile saline soaked gauze pad. Under a dissecting microscope, the ovary was allowed for the insertion of a 30 gauge needle into the bursa. Suspension ($1\times10^6$) of OVCAR-3/luc cells in a maximum volume of 20 mL was slowly injected between the bursa and the ovary. After the reproductive tract and fat pad was replaced back into the peritoneal cavity, the abdominal wall was closed with wound clips. Wound clips were removed 7 or more days post-surgery.

Growth of tumor was monitored by bioluminescence imaging (BLI) using in vivo imaging system (Caliper Life Sciences). BLI signals came from the activity of luciferase expressed by the implanted OVCAR-3/luc cells. Prior to being monitored, the tumor-implanted mice were injected intraperitoneally with 150 mg/kg of D-luciferin substrate. The Regions of Interest (ROIs) in tumor area were selected and used for quantification of tumor size by the software provided by the Caliper Life Sciences. Volumes or sizes of ROIs were calculated as $L\times W^2/2$, where L was the largest and W was the smallest diameter of each ROI. The ROI size was shown as mean volume±standard deviation from at least three mice.

Histological Staining

Tumors and normal ovaries from mice with different treatments were collected for histological assay after mice were sacrificed. 5 mm paraffin tissue sections were prepared for analysis. Morphology of tumors and normal ovaries were examined by haematoxylin and eosin (H&E) staining. TUNEL staining were used for the live/dead assay in the tissue sections using DeadEnd™ Fluorometric TUNEL System (Promega, USA). Tissue sections were examined at magnification of 400× using fluorescent microscope (Zeiss, Germany).

Statistical Analysis

Data are expressed as mean±standard deviation. The statistical significance was determined by student's test analysis of variance. * indicates $p<0.05$,  indicates $p<0.01$, and * indicates $p<0.001$. P-value of lower than 0.05 was considered statistically significant.

EXAMPLE 1

Figure 2:
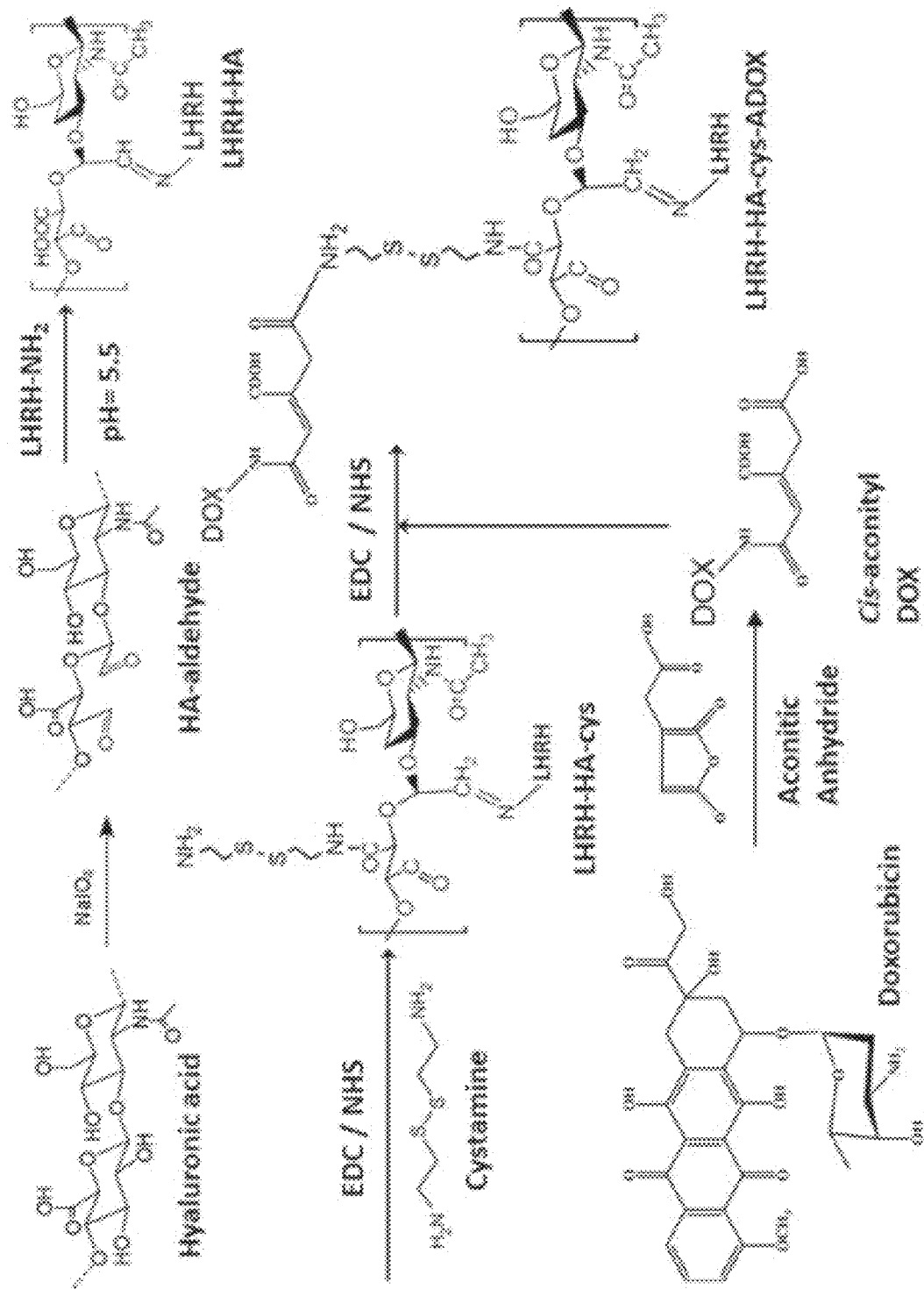
FIG. 2 shows the synthetic route of an exemplary targeted stimuli-responsive polymer-drug conjugate termed LHRH-HA-cys-ADOX, which indicates a conjugate including a LHRH peptide, hyaluronic acid (HA), cystamine, and a drug complex of doxorubicin (DOX) and a cis-aconityl group (referred to as ADOX)

Preparation of the Targeted Stimuli-Responsive Polymer-Drug Conjugate 1.1 Conjugation of an Active Targeting Moiety to a Hydrophilic Polymer This example illustrates the preparation method of the targeted stimuli-responsive polymer-drug conjugate, the forming units of the stimuli-responsive multifunctional nanoparticle of the present invention. An exemplary preparation method is presented in FIG. 2 and detailed in the following paragraphs.

The first step of the preparation method is conjugating covalently an active targeting moiety to a hydrophilic polymer to form a targeted polymer. In one preferred embodiment, the hydrophilic polymer is a smaller-sized cancer-targeting hydrophilic polymer such as hyaluronic acid (HA) with a molecular weight of below 20 kDa; the active targeting moiety is a small molecule such as a peptide with 5-20 amino acid residues.

In the following examples, the active targeting moiety is the LHRH peptide, which may be bound by receptors overexpressed on a variety of cancer cells including ovarian cancer cells and has 10 amino acid residues with the sequence of pyroGlu-His-Trp-Ser-Tyr-Gly-Leu-Arg-Pro-Gly-NH$_2$ (SEQ ID NO:1); the hydrophilic polymer is aldehyde-functionalized HA. To prepare the aldehyde-functionalized HA, 0.1 g of HA with a molecular weight of about 16 kDa and 1 g of sodium metaperiodate were separately dissolved in 10 mL deionized water and mixed together. After the mixed solution was stirred in the dark for 2 hours, it was added with 1 mL of ethylene glycol and stirred for 1 hour to stop the reaction. The resulting solution was dialyzed for one day against deionized water and then lyophilized for subsequent use.

To conjugate the aldehyde-functionalized HA with the LHRH peptide to produce a targeted polymer termed LHRH-HA, 20 mg of aldehyde-functionalized HA was dissolved in sodium acetate buffer (pH 5.5) at a concentration of 5 mg/mL, and the LHRH peptide in the feed ratio of 0.1 was added. The reaction mixture was incubated at room temperature for 24 hours with mild stirring. The product of LHRH-HA was purified from the reaction mixture by dialysis against a large excess of phosphate buffered saline (PBS; sodium chloride 136.9 mM, potassium chloride 2.68 mM, sodium hydrogen phosphate 8.06 mM, and potassium dihydrogen phosphate 1.47 mM, pH 7.4) for one day and lyophilization. The aldehyde groups on HA backbone was quantified with Amplite™ Colorimetric Aldehyde Quantitation Kit (AAT Bioquest, Inc., USA).

1.2 Conjugation of a Redox-Responsive Moiety to the Hydrophilic Polymer of the Targeted Polymer The second step of the preparation method is conjugating covalently a redox-responsive moiety to the hydrophilic polymer of the targeted polymer to form a targeted redox-responsive polymer. In the following examples, the redox-responsive moiety is cystamine (abbreviated as cys), which possesses a redox-responsive linkage of disulfide bond. To modify the HA backbone of the LHRH-HA with cystamine to produce a targeted redox-responsive polymer termed LHRH-HA-cys, 0.2 g of the LHRH-HA was first dissolved in PBS (0.1 M, pH 7.4) for 2 hours to obtain a 4 mg/mL solution, and the solution was added with 2.5 mmol EDC and 1.0 mmol sulfo-NHS and stirred for 15 minutes. Next, 1.12 g of cystamine dihydrochloride (5.0 mmol) was added and the reaction mixture was stirred at room temperature for 6 hours. The product of the LHRH-HA-cys was purified from the reaction mixture by dialysis against 0.1 M NaCl and then against distilled water for one day using a dialysis membrane (MWCO 6000 Da), followed by lyophilization. The lyophilized product was stored at 4° C. A conjugate of HA and cystamine, termed HA-cys, was also prepared according to the abovementioned procedure using HA in place of the LHRH-HA.

1.3 Conjugation of a pH-Responsive Moiety of a Drug Complex to the Redox-Responsive Moiety of the Targeted Redox-Responsive Polymer The third step of the preparation method is conjugating covalently a pH-responsive moiety of a drug complex to the redox-responsive moiety of the targeted redox-responsive polymer to form a targeted stimuli-responsive polymer-drug conjugate. In the following examples, the drug complex includes a hydrophobic anticancer drug doxorubicin (DOX) covalently linked to a cis-aconityl group, which possesses an acid-labile linkage that is hydrolyzed below pH 7. To prepare the drug complex of DOX and the cis-aconityl group, termed cis-aconityl DOX, 10 mg DOX.HCl dissolved in 400 µL of deionized water and 13.46 mg cis-aconitic anhydride in 1 mL of 1,4-dioxane were slowly mixed, and the mixture were stirred overnight at 4° C. The mixture was then mixed 5 mL of chloroform and 5 mL of 5% aqueous sodium bicarbonate solution. The chloroform phase was decanted and the residual solution was extracted with ethyl acetate. The resulting solution was concentrated using a rotary evaporator and dried at room temperature under vacuum.

The cis-aconityl group of the cis-aconityl DOX was conjugated to the amino group of cystamine of the LHRH-HA-cys via the EDC/NHS coupling reaction to produce a targeted stimuli-responsive polymer-drug conjugate termed LHRH-HA-cys-ADOX. More specifically, 100 mg of the LHRH-HA-cys was first dissolved in 10 mL distilled water, followed by dilution with 10 mL of methanol to obtain a polymer solution. A predetermined amount of cis-aconityl DOX was dissolved in 1 mL of dimethylformamide, and equal amounts of EDC and NHS were added into the solution. After stirred for 15 min, the cis-aconityl DOX solution was mixed with the polymer solution and the resulting mixture was stirred at room temperature for one day. The product of the LHRH-HA-cys-ADOX was obtained from the mixture by dialysis against an excess of distilled water and lyophilization. A conjugate of the HA-cys and the cis-aconityl DOX, termed HA-cys-ADOX, was also prepared according to the abovementioned procedure using HA-cys in place of the LHRH-HA-cys.

1.4 Characterization of the HA-cys-ADOX

To verify the successful conjugation of various segments of the targeted stimuli-responsive polymer-drug conjugate and to determine the degree of substitution, the chemical structure of HA, the HA-cys and the HA-cys-ADOX were analyzed by nuclear magnetic resonance (NMR) spectra using Varian uniytinova-500 NMR spectrometer (Varian, USA). The degree of substitution was defined as the number of molecules per 100 unit residues of hyaluronic acid, and it was calculated by the integration ratio between characteristic peaks of hyaluronic acid, cystamine, and cis-aconityl linkage. To prepare samples for NMR analysis, 5 mg of HA, the HA-cys, or the HA-cys-ADOX was dissolved in deuterium oxide ($D_2O$).

Figure 3:
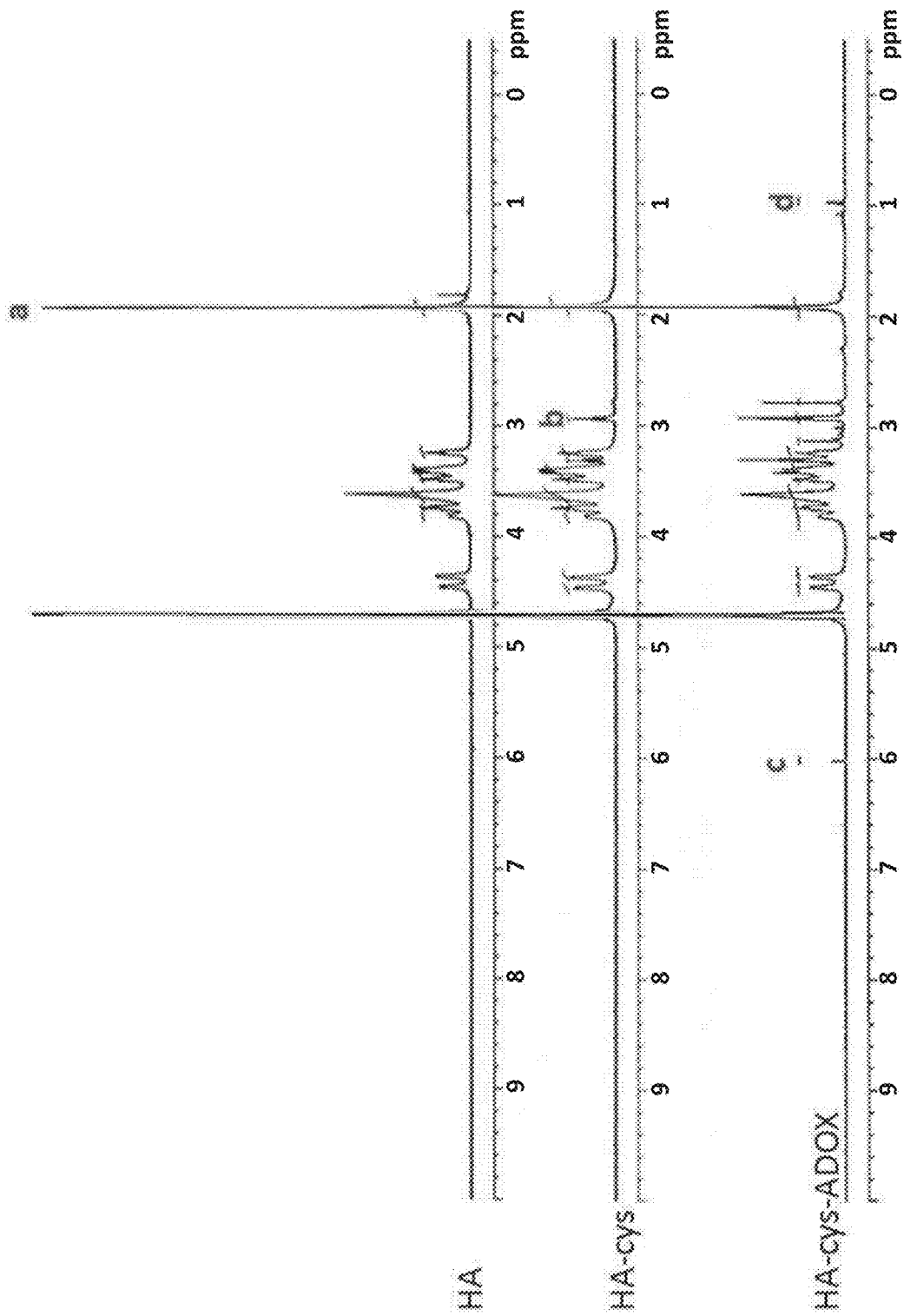
FIG. 3 is a comparison between the $^1$H NMR spectra of HA, a conjugate of HA and cystamine (referred to as HA-cys), and a conjugate of HA, cystamine, and ADOX (referred to as HA-cys-ADOX) from top panel to bottom panel.

The $^1H$ NMR spectra of HA, the HA-cys, and the HA-cys-ADOX are compared in FIG. 3 from top panel to bottom panel. The characteristic methyl peak of acetoamide group on HA, denoted as peak a, was observed at about 2.0 ppm in the spectra of HA, the HA-cys, and the HA-cys-ADOX. The remained proton peaks of HA appeared at 3.3-3.9 ppm and 4.4-4.6 ppm. The characteristic peak of methylene group in cystamine, denoted as peak b, appeared at about 2.85-2.95 ppm in the spectra of the HA-cys and the HA-cys-ADOX. The characteristic peaks of methine group in cis-aconityl linkage and methyl group in DOX, denoted respectively as peaks c and d, respectively, appeared at about 6.0-6.2 ppm and 1.0 ppm in the spectrum of the HA-cys-ADOX. The characteristic peak at 4.8 ppm was resulted from $D_2O$. The results indicate that the targeted stimuli-responsive polymer-drug conjugate may be successfully prepared based on the steps illustrated in this example.

The amount of cystamine and cis-aconityl DOX in the HA-cys-ADOX was quantitatively estimated from the integration ratio between the characteristic peaks. The degree of substitution of cystamine and cis-aconityl DOX was 17.8±4.23% and 6.2±0.4%, respectively. Drug content of DOX was estimated as 10.5±0.24 wt % using the fluorescence spectroscopy. The degree of substitution of the LHRH peptide was 12.1±2.98% estimated by aldehyde assay.

EXAMPLE 2

Preparation and Characterization of the Stimuli-Responsive Multifunctional Nanoparticle This example illustrates preparation of the stimuli-responsive multifunctional nanoparticle via self-assembly of the targeted stimuli-responsive polymer-drug conjugate in an aqueous liquid. For example, to prepare LHRH-HA-cys-ADOX nanoparticles, 5 mg of the LHRH-HA-cys-ADOX was dissolved in 1 mL deionized water. The resulting solution was sonicated for 30 min on ice, followed by filtration through a 0.45 μm pore-sized microporous membrane to eliminate non-assembled conjugates. As a comparative example to the LHRH-HA-cys-ADOX nanoparticle of the present invention, HA-cys-ADOX nanoparticles were also prepared according to the abovementioned procedure using the HA-cys-ADOX for self-assembly.

Particle size and polydispersity index (PDI) of the LHRH-HA-cys-ADOX nanoparticles or the HA-cys-ADOX nanoparticles were estimated by a dynamic light scattering (DLS) using Malvern Zetasizer Nano-ZS90 (Malvern instruments, UK) according to manufacturer's protocol. Moreover, the morphology of the abovementioned nanoparticles was examined by transmission electron microscopy (TEM) using Hitachi H7500 (Hitachi, Japan). To prepare TEM specimen, suspension of the LHRH-HA-cys-ADOX nanoparticles or the HA-cys-ADOX nanoparticles was dropped on carbon-coated copper grids and air-dried at room temperature.

Figure 4A:
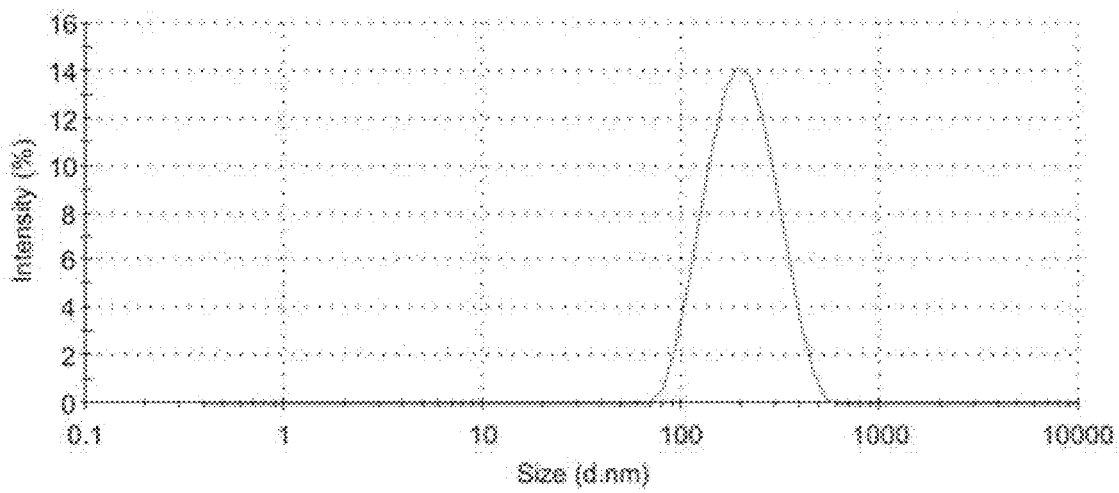
FIGS. 4A-4B show size distribution of the HA-cys-ADOX nanoparticles and the LHRH-HA-cys-ADOX nanoparticles of the present invention, respectively.
Figure 4B:
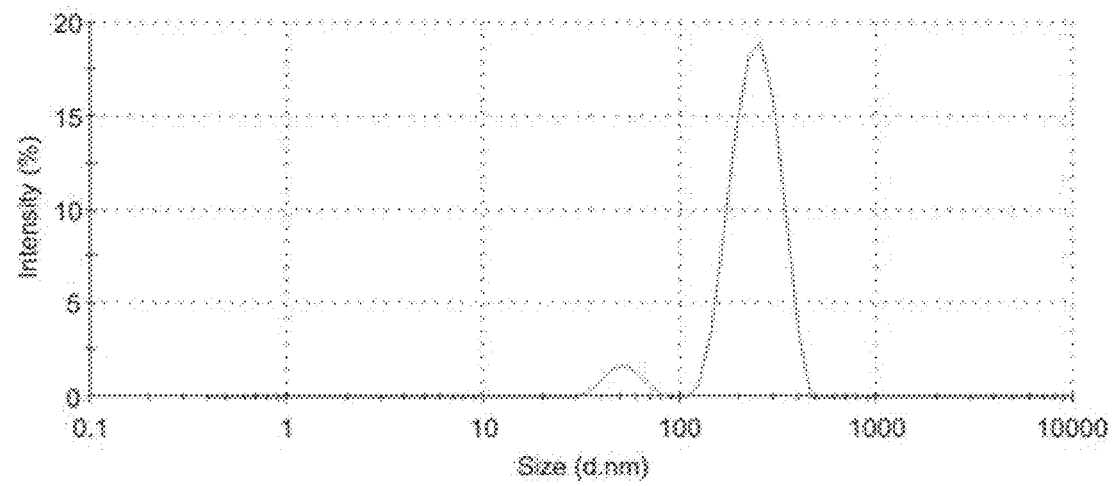
Figure 5A:
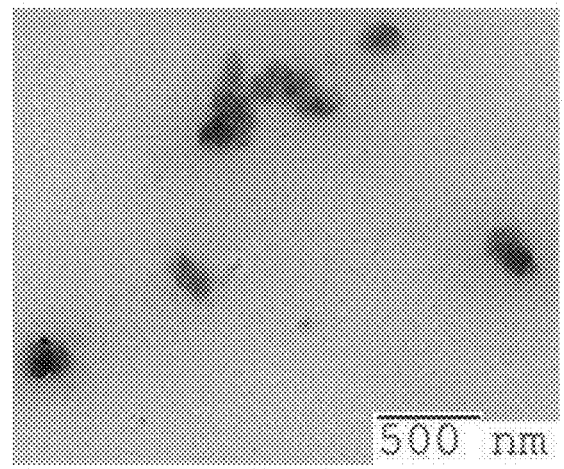
FIGS. 5A-5B show transmission electron microscopy (TEM) images of the HA-cys-ADOX nanoparticles and the LHRH-HA-cys-ADOX nanoparticles of the present invention; the scale bars in FIG. 5A and FIG. 5B represent 500 nm and 100 nm, respectively.
Figure 5B:
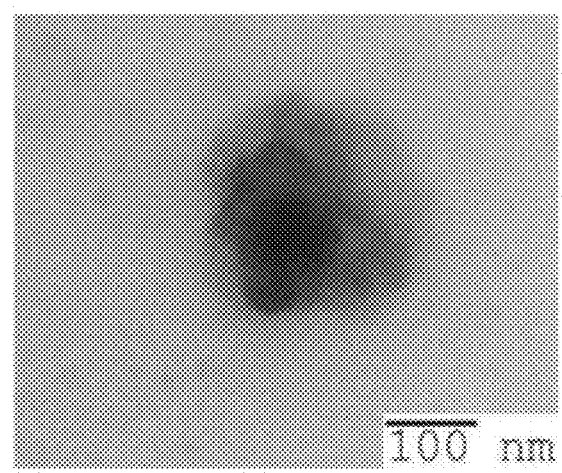
Figure 5C:
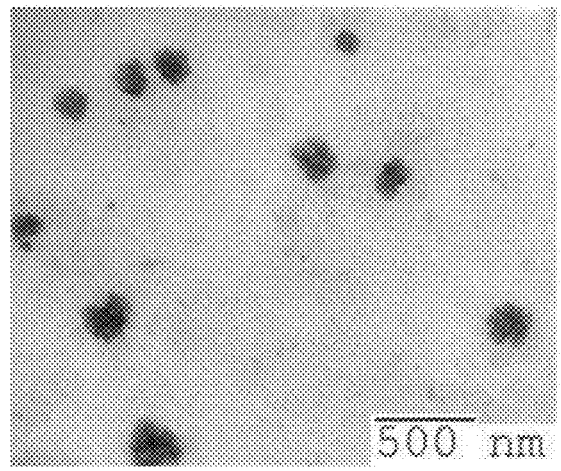
FIGS. 5C-5D show TEM images of the LHRH-HA-cys-ADOX nanoparticles of the present invention; the scale bars in FIG. 5C and FIG. 5D represent 500 nm and 100 nm, respectively.
Figure 5D:
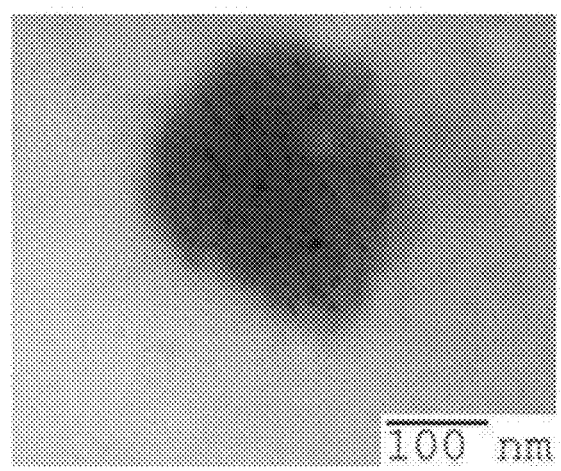

FIGS. 4A-4B show size distribution of the HA-cys-ADOX nanoparticles and the LHRH-HA-cys-ADOX nanoparticles of the present invention, respectively. According to FIGS. 4A-4B, the average sizes of the HA-cys-ADOX nanoparticles and the LHRH-HA-cys-ADOX nanoparticles were 190.1±5.65 nm (PDI=0.221) and 229.0±5.58 nm (PDI=0.414), respectively, suggesting a narrow size distribution. The larger size of the LHRH-HA-cys-ADOX nanoparticles indicated the outwardly extended LHRH peptide on the surface of the nanoparticles.

FIGS. 5A-5B and FIGS. 5C-5D show TEM images at different magnification of the HA-cys-ADOX nanoparticles and the LHRH-HA-cys-ADOX nanoparticles of the present invention, respectively. According to FIGS. 5A-5D, the LHRH-HA-cys-ADOX nanoparticles and the HA-cys-ADOX nanoparticles were spherical in shape and were about 100-150 nm in size. The slightly smaller sizes evaluated by TEM images were due to dehydration of the TEM specimen which caused shrinkage of the nanoparticles. The results of DLS and TEM confirmed that the targeted stimuli-responsive polymer-drug conjugates were able to self-assemble into nanoparticles, and the resulting stimuli-responsive multifunctional nanoparticles of the present invention such as the LHRH-HA-cys-ADOX nanoparticles were stably dispersed in aqueous solutions.

The stimuli-responsive multifunctional nanoparticle of the present invention is able to further encapsulate an imaging agent during the self-assembly process. In one preferred embodiment, the imaging agent is a near-infrared (NIR) fluorescent dye such as cyanine 5.5 (abbreviated as Cy5.5). To prepare Cy5.5-loaded LHRH-HA-cys-ADOX nanoparticles, 5 mg of the LHRH-HA-cys-ADOX and 0.5 mg of Cy5.5 were dissolved in 1 mL deionized water. The resulting solution was sonicated for 30 min on ice, followed by filtration through a 0.45 μm pore-sized microporous membrane to eliminate non-assembled conjugates. The ratio by weight of the LHRH-HA-cys-ADOX and Cy5.5 preferably ranged from 10:1 to 15:1. As a comparative example to the Cy5.5-loaded LHRH-HA-cys-ADOX nanoparticle of the present invention, Cy5.5-loaded HA-cys-ADOX nanoparticles were prepared according to the abovementioned procedure using the HA-cys-ADOX for self-assembly.

The Cy5.5 loading content of (weight of the encapsulated Cy5.5/weight of the Cy5.5-loaded nanoparticle×100%) and Cy5.5 loading efficiency (the amount of the encapsulated Cy5.5/the amount of Cy5.5 feeding×100%) were determined using a visible-ultraviolet spectrophotometer. It showed that the Cy5.5 loading content and Cy5.5 loading efficiency of the Cy5.5-loaded LHRH-HA-cys-ADOX nanoparticles were 8±0.8 wt % and 81.6±8.1%, respectively.

EXAMPLE 3

In Vitro Drug Release Profile of the Stimuli-Responsive Multifunctional Nanoparticle To analyze the drug release profiles of the stimuli-responsive multifunctional nanoparticle of the present invention under conditions of different pH and redox potential, dialysis method was used to evaluate cumulative drug release from the exemplary HA-cys-ADOX nanoparticles, since the HA-cys-ADOX nanoparticles and the LHRH-HA-cys-ADOX nanoparticles of the present invention only differed by the absence or presence of the LHRH peptide for active targeting. For the analysis, the HA-cys-ADOX was dissolved in PBS at the concentration of 2 mg/mL, followed by sonication for 30 min to form a solution of the HA-cys-ADOX nanoparticles. Next, 500 μl of the solution was placed into a cellulose membrane tube and immersed in a vial of 20 ml PBS. The pH and redox potential of the PBS was pre-adjusted with hydrochloric acid or dithiothreitol (DTT) to create an acidic (pH 5.0) or reductive (25 mM DTT) condition. The immersed cellulose membrane tube was then incubated at 37° C. under gentle stirring. The whole PBS was replaced with fresh pre-adjusted PBS at predetermined time points for maintenance of the acidic or reductive condition and determination of the amount of the released DOX. The released DOX was quantified using the fluorescence spectrometer, and the DOX spectrum was obtained with an excitation wavelength at 490 nm and an emission wavelength at 535 nm. The experiment was repeated four times.

Figure 6:
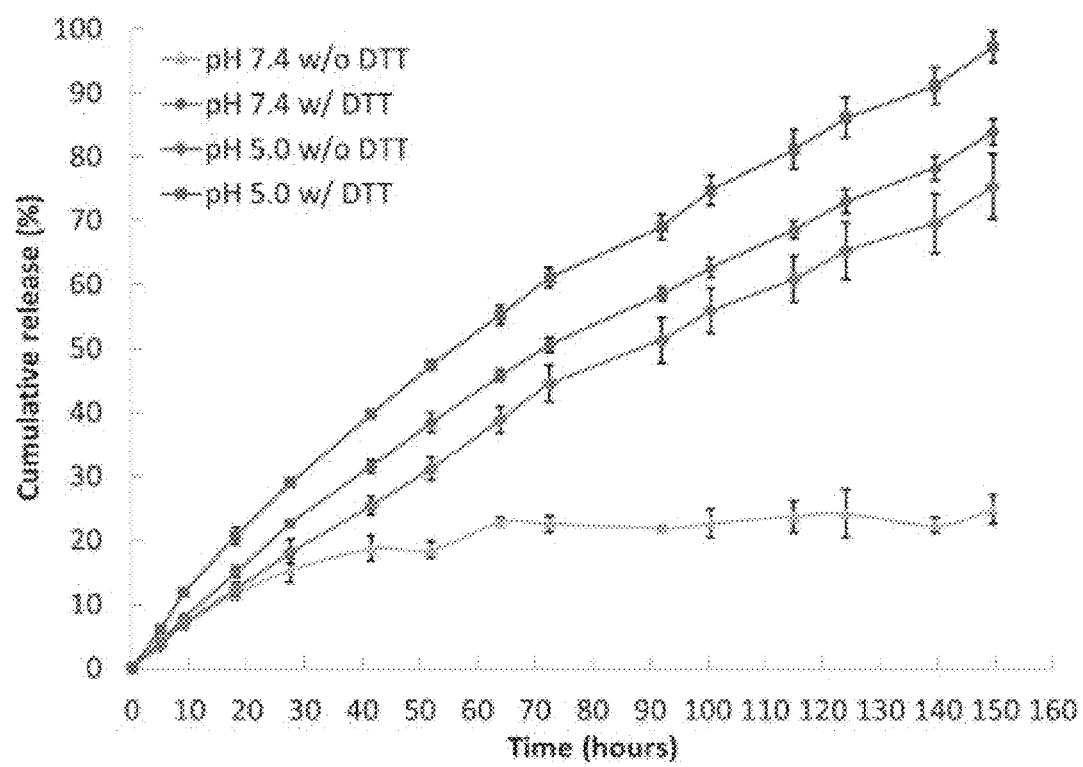
FIG. 6 shows in vitro drug release profiles of the HA-cys-ADOX nanoparticles under conditions of different pH and redox potential.

According to FIG. 6, under the condition of neutral pH and without DTT (pH 7.4 w/o DTT), the HA-cys-ADOX nanoparticles showed a biphasic drug release pattern with an initial burst release of less than 20% DOX within 48 hours, followed by no further release for more than 100 hours. However, under the condition of neutral pH and with DTT (pH 7.4 w/DTT), the cumulative release of DOX was about 80% after dialysis for 150 hours. Similarly, under the condition of pH 5.0 and without DTT, the cumulative release of DOX reached about 70% at 150 hours. Comparatively, the combination of acidic and reductive conditions (pH 5.0 and with DTT) stimulated significantly more DOX release, leading to the cumulative release of 95% at 150 hours. These data demonstrated that drug release from the stimuli-responsive multifunctional nanoparticle was increased in response to decreasing pH and increasing reductive potential, indicating that dissolution of the acid-labile linkage in the pH-responsive moiety and cleavage of the disulfide bond in the redox-responsive moiety were critical to the controlled and complete drug release in intracellular environment. The results also showed that the stimuli-responsive multifunctional nanoparticle of the present invention possessed long-term stability up to 150 hours and prevented significant amounts of premature drug release under physiological conditions.

EXAMPLE 4

Cellular Uptake of the Stimuli-Responsive Multifunctional Nanoparticle

The cellular uptake of the stimuli-responsive multifunctional nanoparticle of the present invention and the intracellular drug delivery were investigated by fluorescence microscopy. Human ovarian cancer cells OVCAR-3 and mouse embryonic fibroblasts NIH3T3 were cultured to 70-80% confluence and seeded onto 4-well chamber slides (BD Falcon, USA) at a density of $1\times10^5$ cells/well. After incubation at 37° C. for 24 hours, DOX.HCl, the HA-cys-ADOX nanoparticles (referred to as HA NPs), or the LHRH-HA-cys-ADOX nanoparticles (referred to as LHRH NPs) dissolved in DMEM at concentrations equivalent to 50 mg/mL DOX was added to the cells for a 2-hour incubation at 37° C. Cells treated with DMEM were the negative control group (NC). Next, fluorescent dyes Lysotracker Green and DAPI in DMEM were sequentially added to the abovementioned cells to stain endosome/lysosome for 2 hours and nuclei for 1 hour. After all the reagents were removed, the cells were washed with PBS (pH 7.4) three times, followed by addition of a mounting medium to fix the cells and prevent fluorescence fading. Cells were examined using a fluorescent microscope (Zeiss, Germany).

Figure 7A:
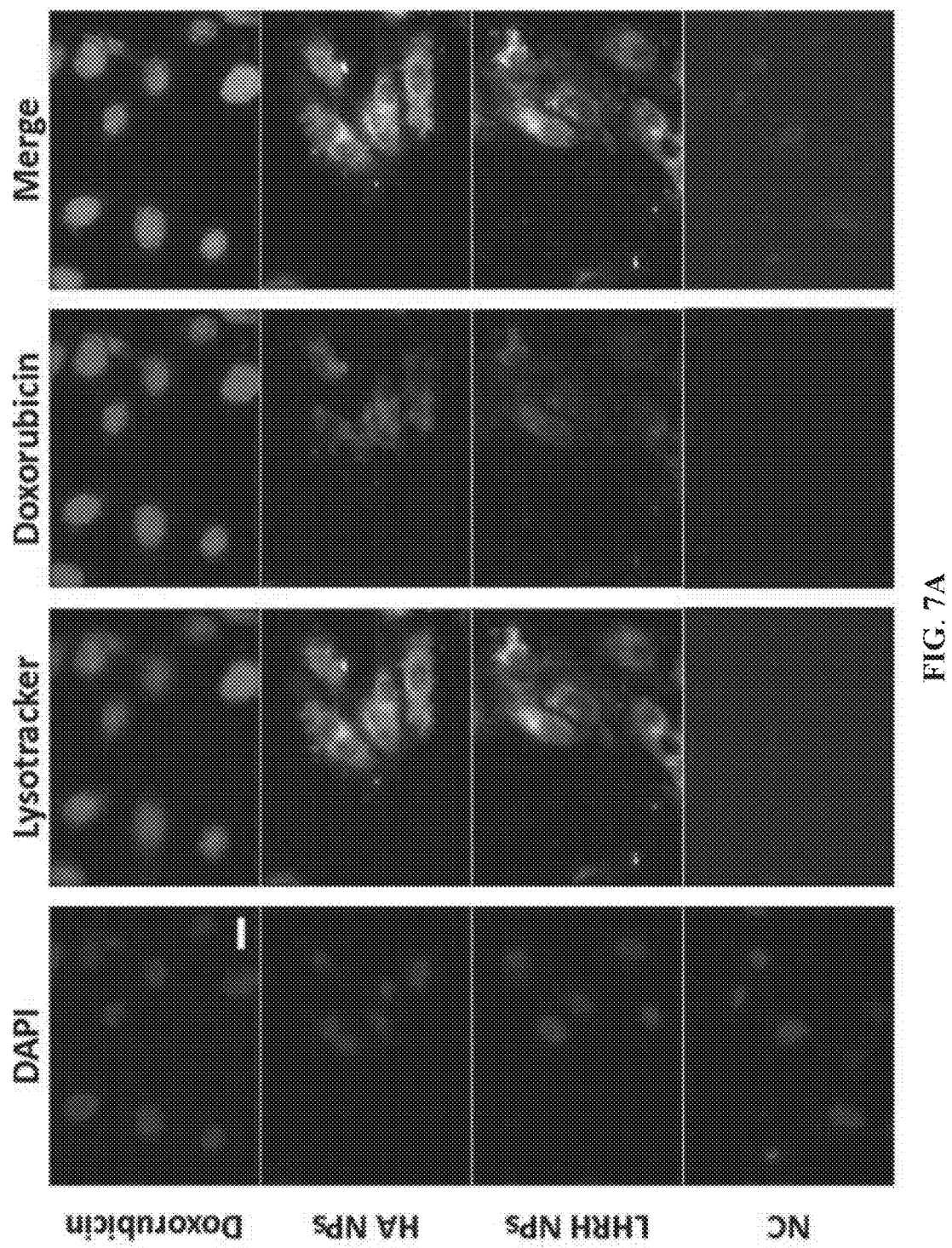
FIG. 7A shows fluorescence micrographs of the OVCAR-3 cells treated for 4 hours with free doxorubicin, the HA-cys-ADOX nanoparticles (referred to as HA NPs), the LHRH-HA-cys-ADOX nanoparticles (referred to as LHRH NPs), or cell culture medium DMEM (negative control group, denoted as NC); the scale bar represents 20 μm.
Figure 7B:
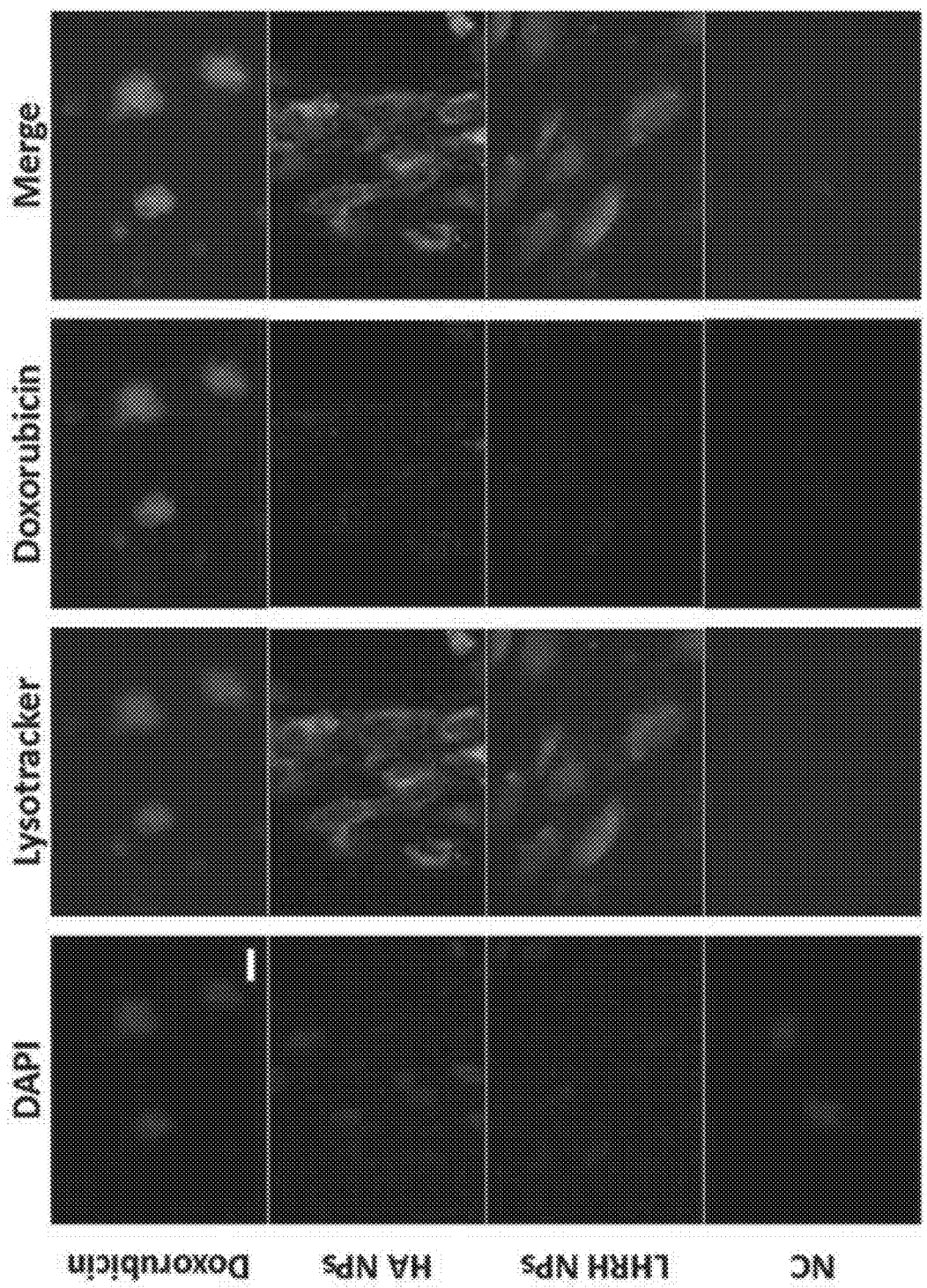
FIG. 7B shows fluorescence micrographs of the NIH3T3 cells treated for 4 with free doxorubicin, the HA-cys-ADOX nanoparticles (HA NPs), the LHRH-HA-cys-ADOX nanoparticles (LHRH NPs), or DMEM (negative control group, denoted as NC); the scale bar represents 20 μm.

As shown in FIG. 7A, after OVCAR-3 cells were treated with the HA NPs or the LHRH NPs for 4 hours, most of the DOX fluorescence was overlapped with the Lysotracker fluorescence. The intensity of DOX fluorescence was significantly increased upon treatment with the LHRH NPs. On the contrary, as shown in FIG. 7B, when NIH3T3 cells were treated with the HA NPs or the LHRH NPs for 4 hours, intracellular DOX fluorescence was of low intensity. Moreover, there was no difference in the intensity of intracellular DOX fluorescence between the OVCAR-3 and the NIH3T3 cells treated with free DOX. These results reveal that administration of free hydrophobic drug would cause drug diffusion into cells without differentiation among normal and cancer cells. However, the stimuli-responsive multifunctional nanoparticle of the present invention can deliver drugs specifically to the cancer cells because of the cancer-targeting hydrophilic polymers such as hyaluronic acid and the active targeting moiety such as the LHRH peptide.

EXAMPLE 5

Cytotoxicity and Anticancer Effect of the Stimuli-Responsive Multifunctional Nanoparticle The cytotoxicity and anticancer effect of the stimuli-responsive multifunctional nanoparticle of the present invention was evaluated by cell viability assay in NIH3T3 and OVCAR-3 cells. The cells were seeded in a 96-well plate at a density of $5\times10^3$ cells/well and incubated at 37° C. for 24 hours. Next, DOX.HCl, the HA-cys-ADOX nanoparticles, or the LHRH-HA-cys-ADOX nanoparticles dissolved in DMEM at predetermined concentrations equivalent to DOX was added to the cells. Cells treated with DMEM were the negative control group. After incubation at 37° C. for 48 hours, the cells were washed with PBS (pH 7.4). Cell viability was measured by MTS assay (CellTiter 96® AQueous One Solution Cell Proliferation Assay (Promega, USA)) according to the manufacturer's instructions and calculated as the ratio of light absorbance at 570 nm of the experimental group to that of the negative control group.

Figure 8A:
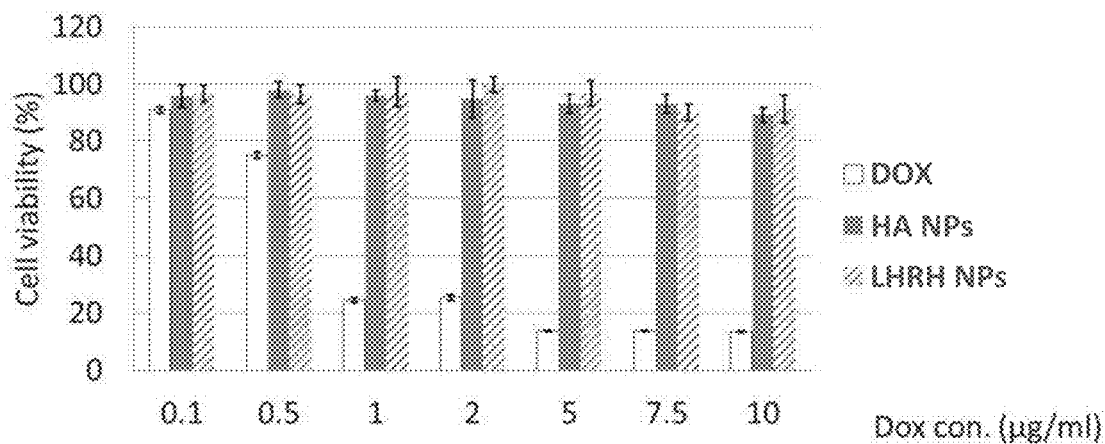
FIGS. 8A-8B show cell viability of the NIH3T3 cells and the OVCAR-3 cells, respectively, treated for 48 hours with various concentrations of free DOX, the HA-cys-ADOX nanoparticles (HA NPs), or the LHRH-HA-cys-ADOX nanoparticles (LHRH NPs) of the present invention.
Figure 8B:
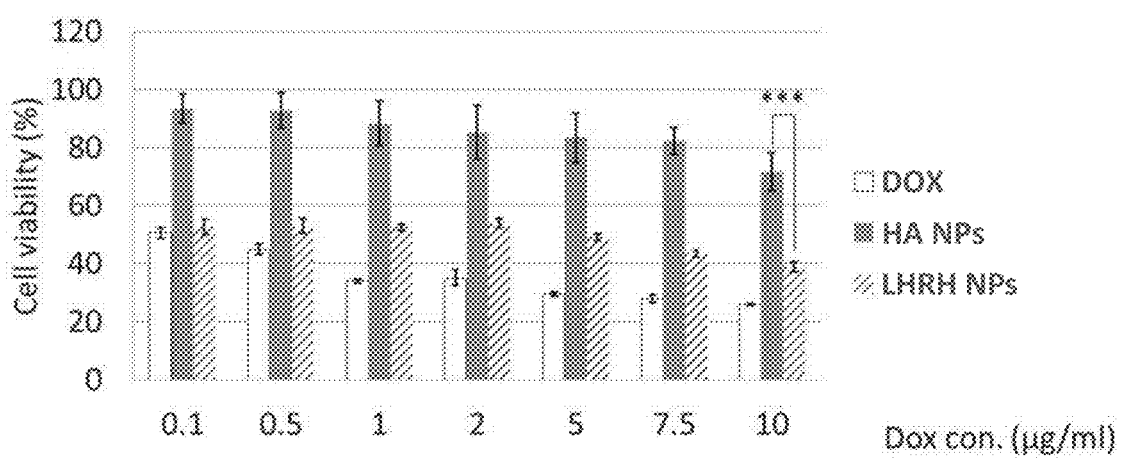

FIG. 8A and FIG. 8B show cell viability of the NIH3T3 cells and the OVCAR-3 cells, respectively, treated for 48 hours with various concentrations of free DOX, the HA-cys-ADOX nanoparticles (HA NPs), or the LHRH-HA-cys-ADOX nanoparticles (LHRH NPs) of the present invention. According to FIGS. 8A-8B, the cytotoxicity of free DOX to both NIH3T3 and OVCAR-3 cells was dose-dependent. However, the HA NPs and the LHRH NPs exhibited much less cytotoxicity to NIH3T3 cells. The NIH3T3 cells maintained viability over 90% even when treated with increasing concentrations of the HA NPs or the LHRH NPs. Though the anticancer effect of the HA NPs on OVCAR-3 cells was greatly diminished when compared with free DOX, the LHRH NPs preserved prominent anticancer effect and dose-dependency. After treated for 48 hours with the LHRH NPs at the concentration equivalent to 10 mg/mL DOX, the viability of OVCAR-3 cells was decreased to less than 40%.

Figure 8C:
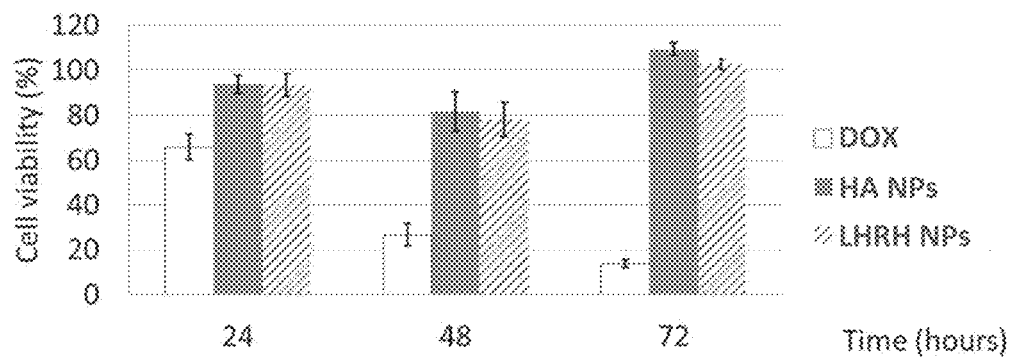
FIGS. 8C-8D show cell viability of NIH3T3 cells and the OVCAR-3 cells, respectively, treated with free DOX, the HA-cys-ADOX nanoparticles (HA NPs), or the LHRH-HA-cys-ADOX nanoparticles (LHRH NPs) of the present invention for 24, 48, and 72 hours.
Figure 8D:
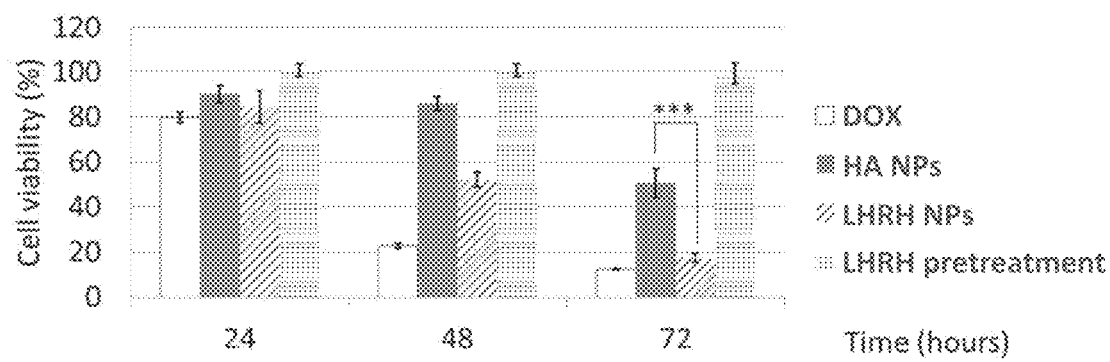

FIGS. 8C and 8D show cell viability of NIH3T3 cells and the OVCAR-3 cells, respectively, treated with free DOX, the HA NPs, or the LHRH NPs of the present invention at the concentration equivalent to 5 µg/ml DOX for 24, 48, and 72 hours. According to FIGS. 8C-8D, the little cytotoxicity of the HA NPs or the LHRH NPs to NIH3T3 cells did not increase with time. However, the anticancer effect of the HA NPs or the LHRH NPs on OVCAR-3 cells was time-dependent and maintained for at least 72 hours. At 72 hour, the anticancer effect of the LHRH NPs was even comparable to free DOX. FIG. 8D also shows that pretreatment of the OVCAR-3 cells with 5 mg/mL of the LHRH peptide for 2 hours in a competing test decreased the anticancer effect of the LHRH NPs, indicating the critical role of the LHRH peptide in the specific cellular uptake and the anticancer effect of the LHRH NPs of the present invention. These results shows that the stimuli-responsive multifunctional nanoparticle of the present invention is highly specific for cancer cells and capable of preserving the therapeutic effects of the encapsulated hydrophobic drugs, while it is of low toxicity to normal cells and thus may cause less unwanted side effects upon administration.

EXAMPLE 6

In Vivo Anti-Tumor Effect and Biodistribution of the Stimuli-Responsive Multifunctional Nanoparticle To evaluate the therapeutic and diagnostic efficacy of the stimuli-responsive multifunctional nanoparticle of the present invention, an orthotopic ovarian tumor xenograft model in nude mice was established by implantation of luciferase-transfected human OVCAR-3 cells (OVCAR-3/luc cells) into mouse ovary. The mice bearing ovarian tumors were then divided into four groups with three mice in each group. Each of the four groups was administered, via the tail vein, with DOX.HCl, the Cy5.5-loaded HA-cys-ADOX nanoparticles (referred to as HA-NPs/Cy5.5), or the Cy5.5-loaded LHRH-HA-cys-ADOX nanoparticles (referred to as LHRH- NPs/Cy5.5) at a dose equivalent to 5 mg/kg of DOX, or PBS at day 0, 5, 10, 15, and 20 after the implantation surgery. For determination of the tumor size of the luciferase-expressing tumors deep within the peritoneal cavity of these mice, bioluminescence imaging (BLI) was conducted 4 hours after drug administration. ROIs (Regions of Interest) in tumor area were selected for calculating the ROI size as an indicator of tumor size.

Figure 9:
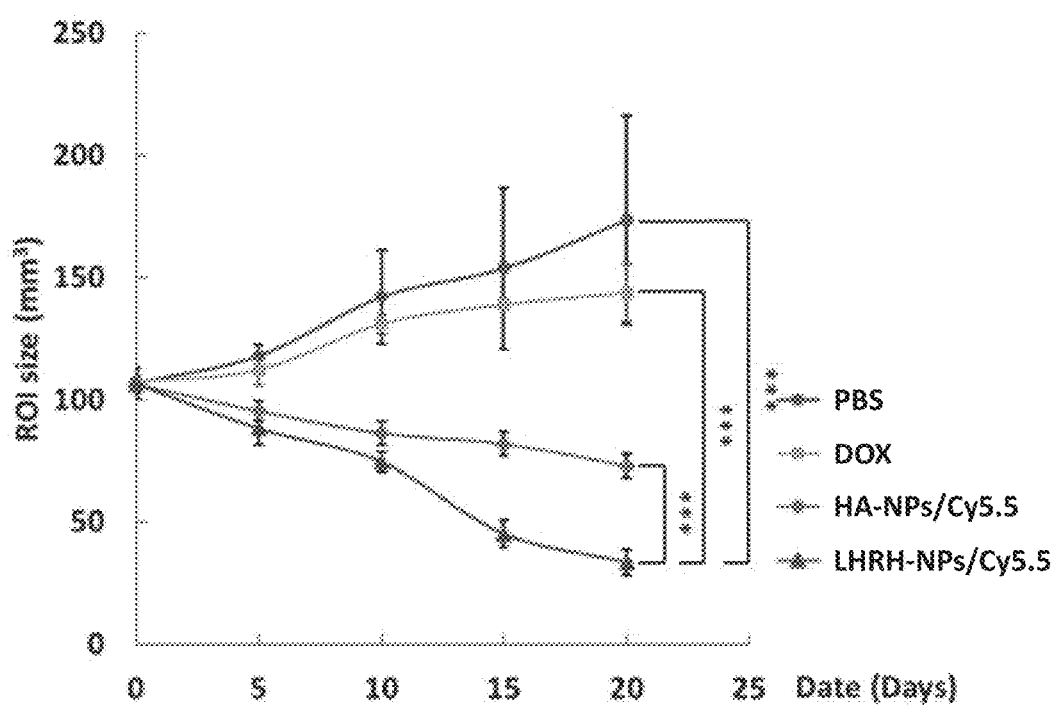
FIG. 9 shows sizes of Regions of Interest (ROI) in tumor area of the tumor-bearing mice after treatment with free DOX, the Cy5.5-loaded HA-cys-ADOX nanoparticles (referred to as HA-NPs/Cy5.5), the Cy5.5-loaded LHRH-HA-cys-ADOX nanoparticles (referred to as LHRH-NPs/Cy5.5) of the present invention, or phosphate buffered saline (PBS)

FIG. 9 shows ROI sizes of the tumor-bearing mice receiving the abovementioned four different treatments. According to FIG. 9, the LHRH-NPs/Cy5.5 and the HA-NPs/Cy5.5 were significantly more effective to inhibit tumor growth than free DOX. Among the two nanoparticles, the LHRH-NPs/Cy5.5 with the active targeting LHRH peptide exhibited greater anti-tumor effect than the HA-NPs/Cy5.5. At day 20, the ROI size of the LHRH-NPs/Cy5.5-treated mice decreased to about 30% of the original size at the beginning of the treatment. Comparatively, the ROI sizes of the mice treated with PBS, free DOX, and the HA-NPs/Cy5.5 were 5.2-fold, 4.3-fold, and 2.2-fold, respectively, greater than that of the LHRH-NPs/Cy5.5-treated mice.

Figure 10:
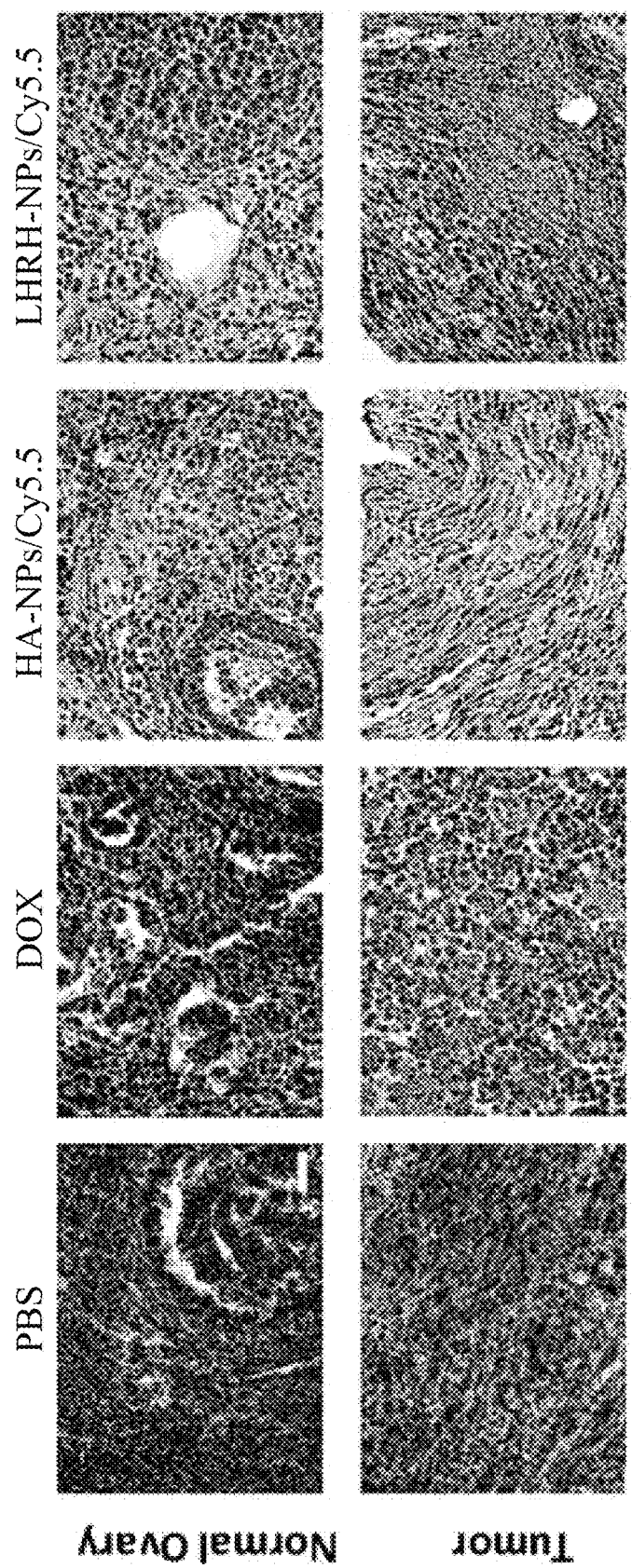
FIG. 10 shows haematoxylin and eosin (H&E) staining images of the sections of the mouse normal ovaries and ovarian tumors treated with free DOX, the Cy5.5-loaded HA-cys-ADOX nanoparticles (HA-NPs/Cy5.5), the Cy5.5-loaded LHRH-HA-cys-ADOX nanoparticles (LHRH-NPs/Cy5.5) of the present invention, or PBS.
Figure 11:
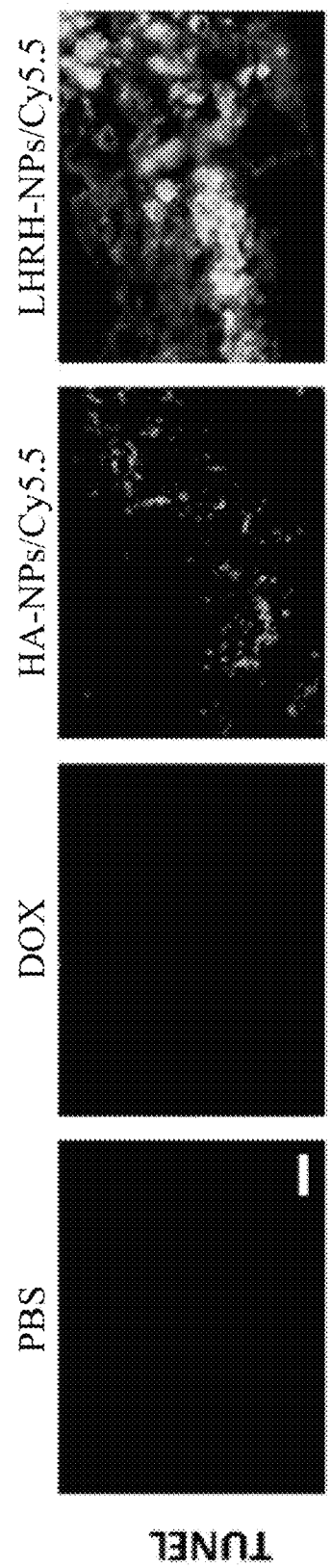
FIG. 11 shows TUNEL staining images of the sections of the mouse ovarian tumors treated with free DOX, the Cy5.5-loaded HA-cys-ADOX nanoparticles (HA-NPs/Cy5.5), the Cy5.5-loaded LHRH-HA-cys-ADOX nanoparticles (LHRH-NPs/Cy5.5) of the present invention, or PBS.

The therapeutic effect of the stimuli-responsive multifunctional nanoparticle of the present invention on ovarian cancer cells was further analyzed histologically after the mice were treated differently as mentioned above for 20 days and sacrificed. FIG. 10 shows H&E staining images of the sections of the mouse normal ovaries and ovarian tumors. FIG. 11 shows TUNEL staining images of the sections of the mouse ovarian tumors. According to FIG. 10, the tumors treated with PBS and free DOX presented similar cell morphology, showing cell proliferation with dense nuclei in random pattern, a typical histologic feature of rapidly growing tumors. However, the tumors treated with the HA-NPs/Cy5.5 and the LHRH-NPs/Cy5.5 appeared more like normal ovary with less proliferative cells. According to FIG. 11, no significant TUNEL fluorescence signal, which marked apoptotic cells, was observed in the tumors treated with PBS and free DOX. In contrast, the tumors treated with the HA-NPs/Cy5.5 and the LHRH-NPs/Cy5.5 exhibited obvious fluorescent signals. The highest fluorescence intensity was found in the LHRH-NPs/Cy5.5-treated tumor.

The results of the BLI and the histological staining demonstrated that the stimuli-responsive multifunctional nanoparticle of the present invention exhibited prominent anti-tumor effect in animals, indicating the successful delivery of the hydrophobic drug to tumors through blood circulation by the stimuli-responsive multifunctional nanoparticle including active targeting moiety. The results also indicated that the acidic and reductive microenvironment of the tumors triggered the effective release of the hydrophobic drug in cancer cells and resulted in the significant inhibition of tumor growth.

The diagnostic efficacy of the stimuli-responsive multifunctional nanoparticle of the present invention was assessed by monitoring biodistribution of the LHRH-NPs/Cy5.5 or the HA-NPs/Cy5.5 in the mice previously described using near-infrared (NIR) optical imaging (excitation wavelength at 675 nm/emission wavelength at 720 nm). The NIR imaging was conducted in vivo for the mice or ex vivo for the tumor-implanted ovaries (also termed tumor side ovaries) and the major organs isolated from the sacrificed mice.

Figure 12A:
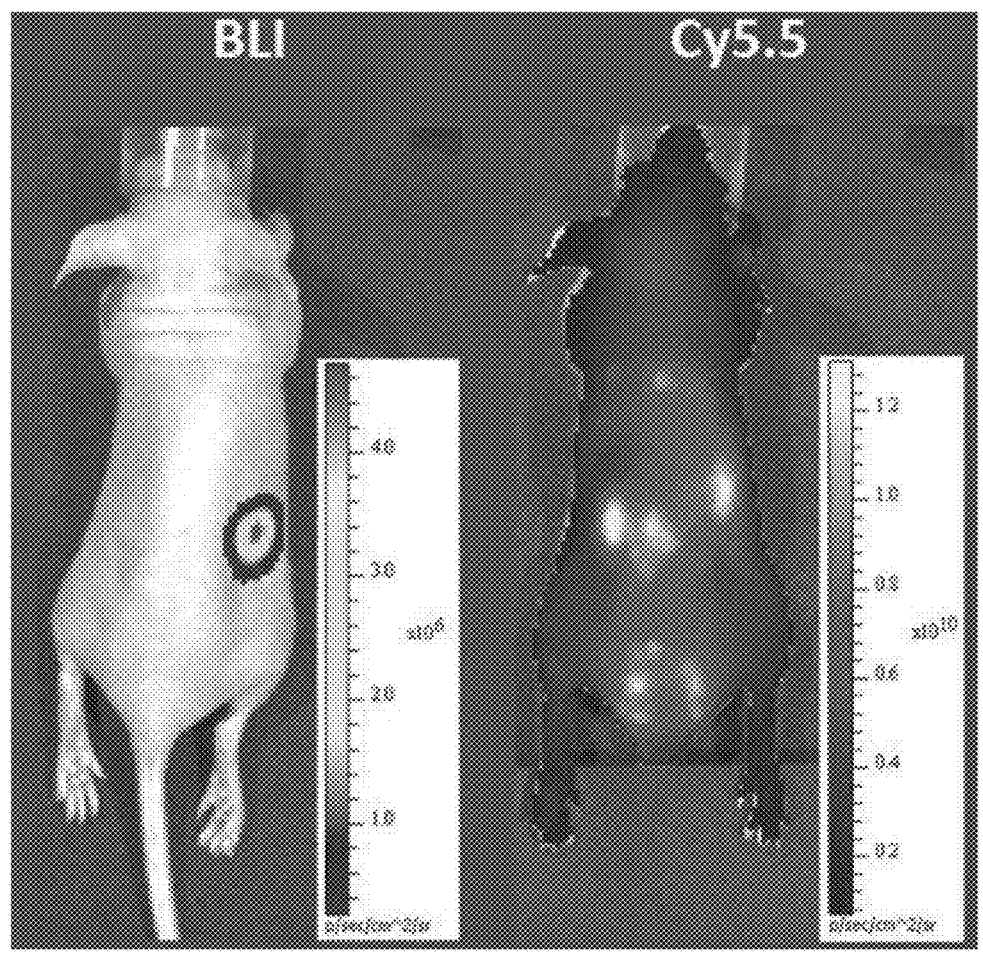
FIG. 12A shows an image of bioluminescence imaging (BLI) and a Cy5.5 fluorescence image of the tumor-bearing mice at 4 hours post-administration of the Cy5.5-loaded HA-cys-ADOX nanoparticles; the scale bars present the intensity of signals.
Figure 12B:
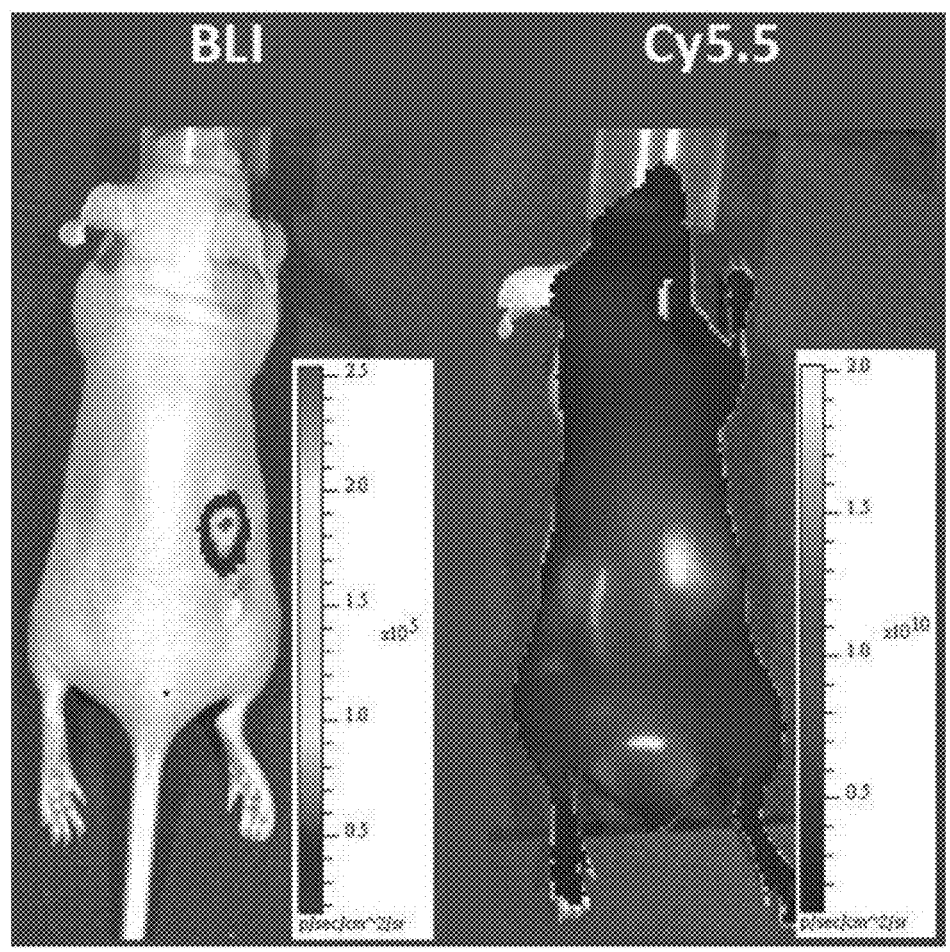
FIG. 12B shows a BLI image and a Cy5.5 fluorescence image of the tumor-bearing mice at 4 hours post-administration of the Cy5.5-loaded LHRH-HA-cys-ADOX nanoparticles of the present invention; the scale bars present the intensity of signals.
Figure 12C:
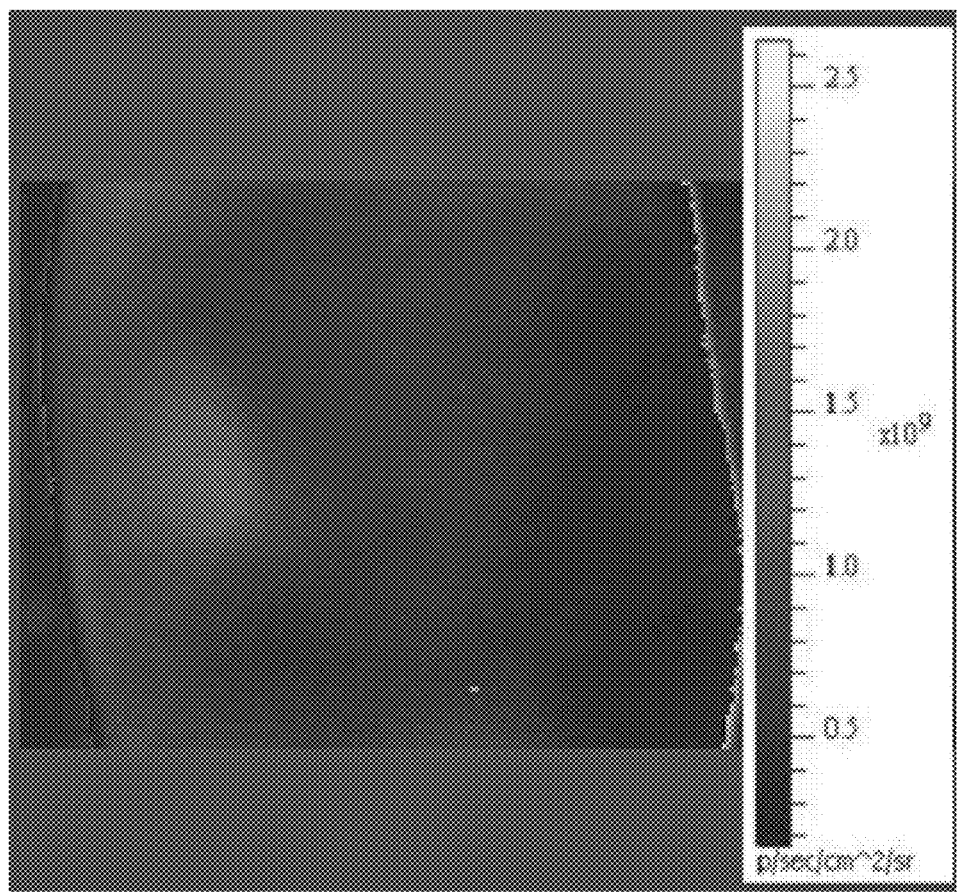
FIG. 12C shows a Cy5.5 fluorescence image from the lateral view of a tumor-bearing mouse at 24 hours post-administration of the Cy5.5-loaded HA-cys-ADOX nanoparticles; the scale bar presents the intensity of signal.
Figure 12D:
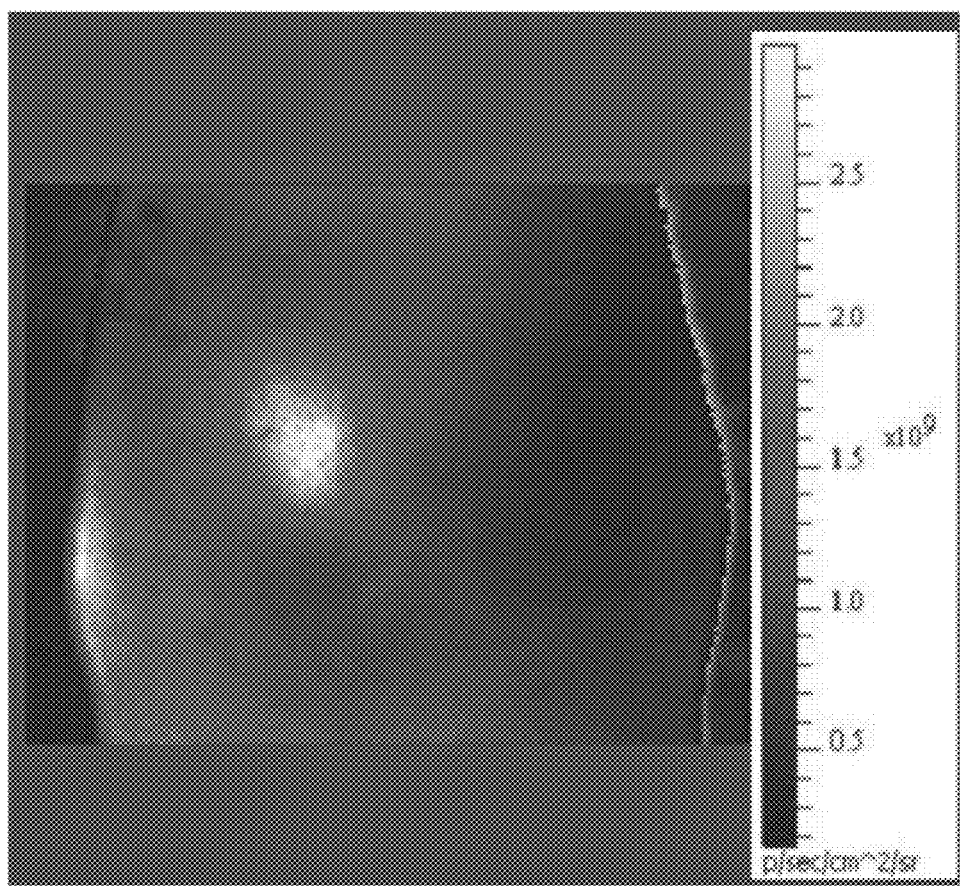
FIG. 12D shows a Cy5.5 fluorescence image from the lateral view of a tumor-bearing mouse at 24 hours post-administration of the Cy5.5-loaded LHRH-HA-cys-ADOX nanoparticles of the present invention; the scale bar presents the intensity of signal.

FIGS. 12A-12B show BLI images and Cy5.5 fluorescence images of the tumor-bearing mice at 4 hours post-administration of the HA-NPs/Cy5.5 and the LHRH-NPs/Cy5.5 of the present invention, respectively. FIG. 12C-12D show Cy5.5 fluorescence images from the lateral view of the tumor-bearing mice at 24 hours post-administration of the HA-NPs/Cy5.5 and the LHRH-NPs/Cy5.5 of the present invention, respectively. According to FIGS. 12A-12B, both the HA-NPs/Cy5.5 and the LHRH-NPs/Cy5.5 were excreted through kidney. Most of the Cy5.5 fluorescence was located in the ovarian tumor of the LHRH-NPs/Cy5.5-treated mouse, while Cy5.5 fluorescence was distributed more widely to non-target tissues in the HA-NPs/Cy5.5-treated mouse. Thus, the LHRH-NPs/Cy5.5 treatment led to greater difference in fluorescence intensity between the ovarian tumor and the normal ovary within 4 hours. According to FIGS. 12C-12D, there was significantly higher intensity of Cy5.5 fluorescence in the ovarian tumor region at 24 hour post-administration of the LHRH-NPs/Cy5.5.

Figure 13A:
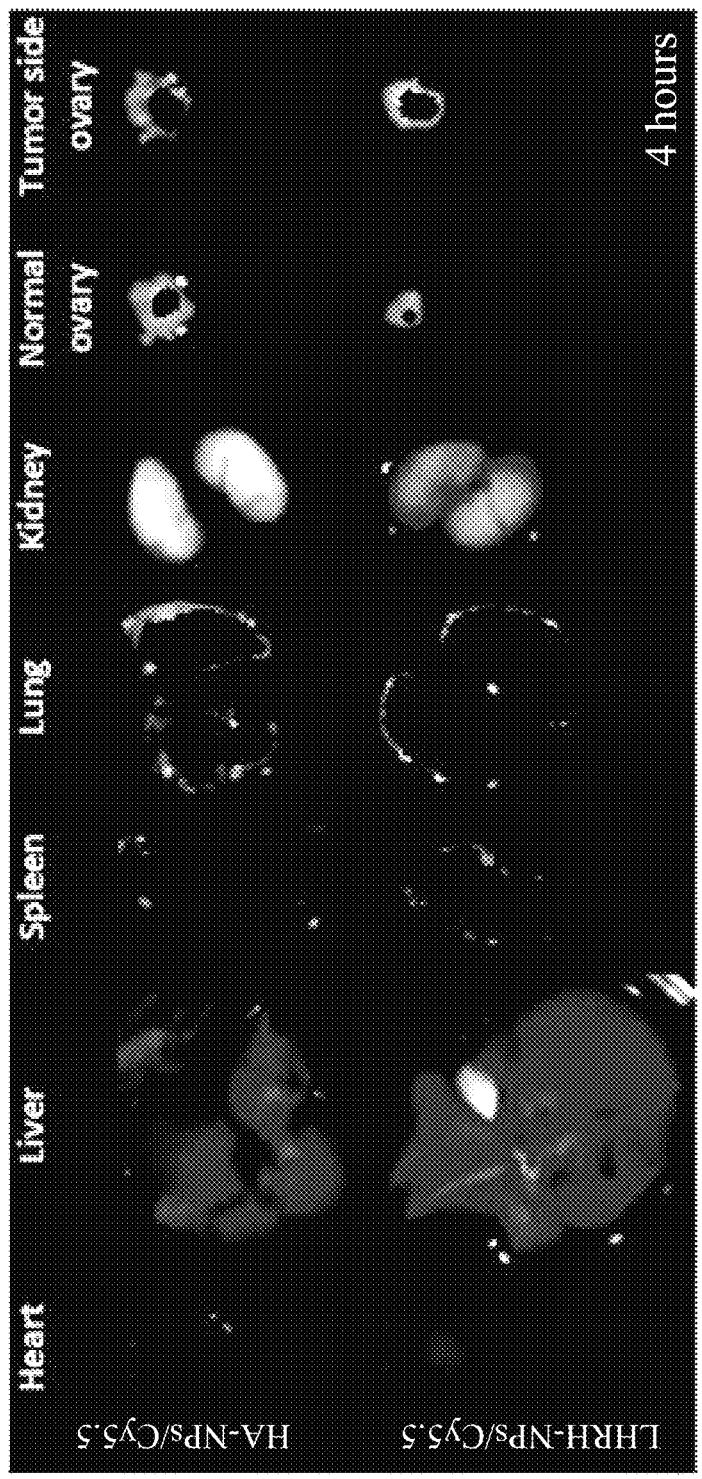
FIGS. 13A-13C show Cy5.5 fluorescence images of the tumor side ovaries and the major organs, including heart, liver, spleen, lung, kidney, and normal ovary, from the mice sacrificed at 4, 24, and 72 hours post-administration of the Cy5.5-loaded HA-cys-ADOX nanoparticles (HA-NPs/Cy5.5) and the Cy5.5-loaded LHRH-HA-cys-ADOX nanoparticles (LHRH-NPs/Cy5.5) of the present invention.
Figure 13B:
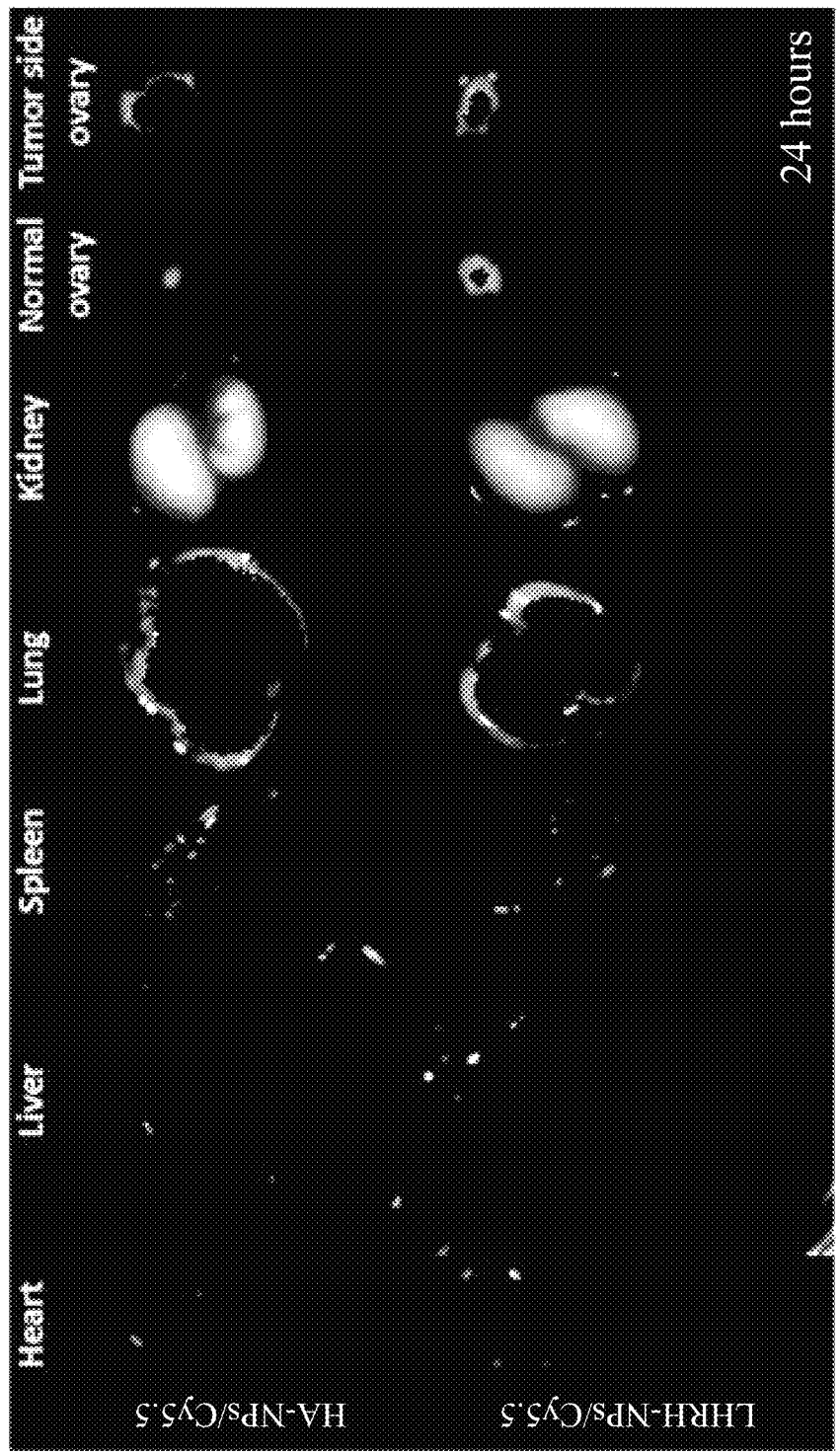
Figure 13C:
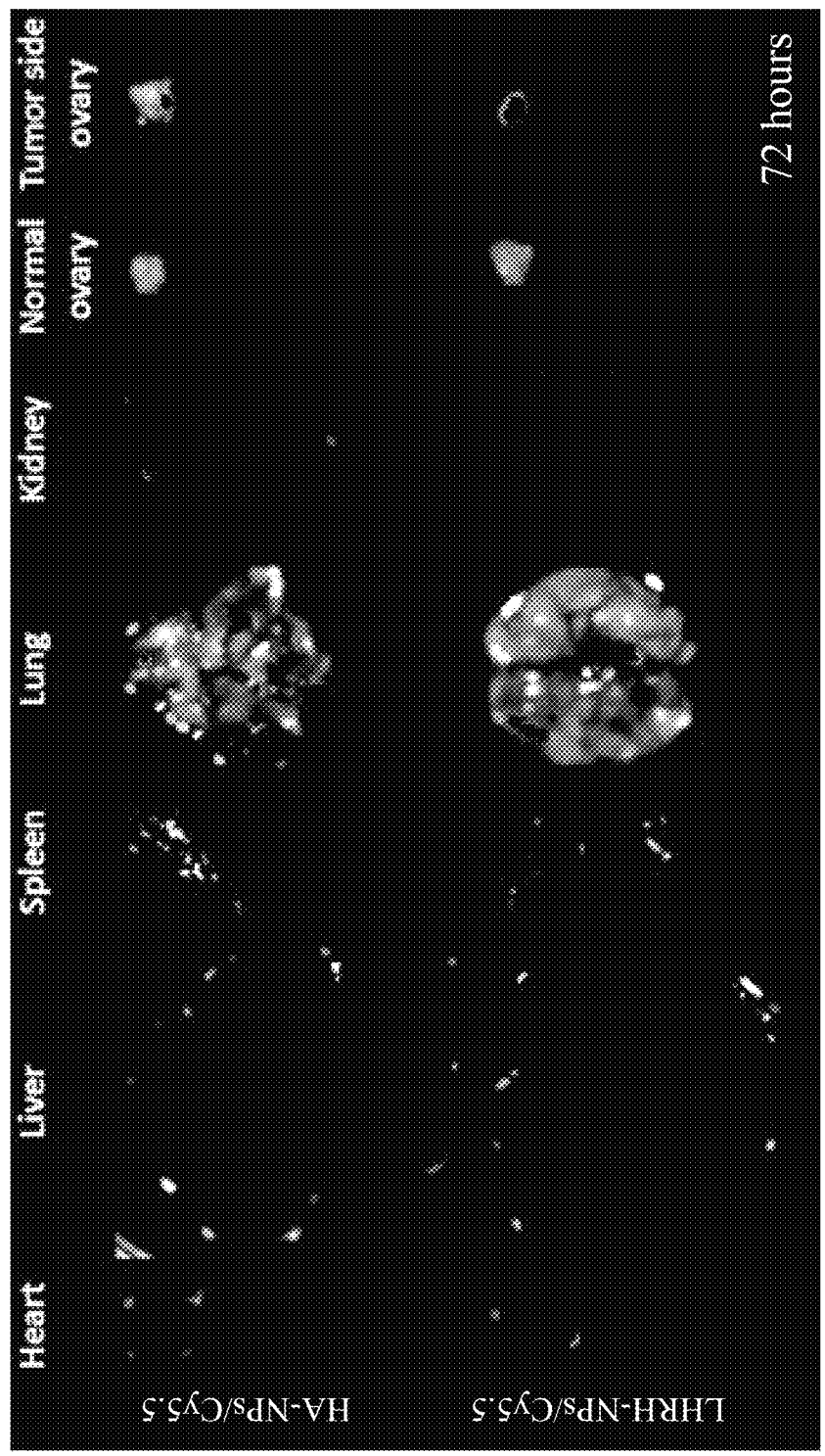

FIGS. 13A-13C show Cy5.5 fluorescence images of the tumor side ovaries and the major organs, including heart, liver, spleen, lung, kidney, and normal ovary, from the mice sacrificed at 4, 24, and 72 hours post-administration of the HA-NPs/Cy5.5 and the LHRH-NPs/Cy5.5 of the present invention. According to FIGS. 13A-13C, Cy5.5 fluorescence was observed in liver and kidney within 24 hours, but the toxicity to these organs was relatively low (data not shown). At 72 hour post-administration, little fluorescence was detected in liver and kidney. In addition, the highest intensity of Cy5.5 fluorescence was observed in the tumor side ovaries of mice treated with LHRH-NPs/Cy5.5 and this fluorescence lasted for at least one day, indicating that the LHRH peptide increased the capability of the LHRH-NPs/Cy5.5 to target ovarian tumors and accumulate therein.

The results of in vivo and ex vivo imaging reveal that the stimuli-responsive multifunctional nanoparticle of the present invention such as the Cy5.5-loaded LHRH-HA-cys-ADOX nanoparticle can specifically accumulate in the site of tumor in animals and successfully deliver imaging agents to tumors for non-invasive in vivo tumor tracking.

In conclusion, the stimuli-responsive multifunctional nanoparticle can be successfully synthesized according to the method of the present invention. The stimuli-responsive multifunctional nanoparticle, when prepared from hydrophilic polymers and active targeting moieties specific for cancer cells, is of low toxicity to normal cells while exerts anticancer effect on cancer cells. Moreover, the pH-responsive and redox-responsive covalent linkages for drug conjugation in the stimuli-responsive multifunctional nanoparticle facilitate not only the stable delivery of hydrophobic drugs and imaging agents in the blood but also the controlled and complete release of these substances in the target cells other than non-target cells. Therefore, the stimuli-responsive multifunctional nanoparticle may enhance the therapeutic effects of the hydrophobic drugs and reduce the side effects, and simultaneously provide diagnostic information.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A method of preparing a stimuli-responsive multifunctional nanoparticle, comprising in sequence the steps of:
   (a) conjugating covalently an active targeting moiety to a hydrophilic polymer to form a targeted polymer at acidic pH, wherein the active targeting moiety is a peptide specific for cancer cells and the hydrophilic polymer is hyaluronic acid;
   (b) conjugating covalently a redox-responsive moiety to the hydrophilic polymer of the targeted polymer to form a targeted redox-responsive polymer, wherein the redox-responsive moiety comprises a disulfide bond;
   (c) conjugating covalently a pH-responsive moiety of a drug complex to the redox-responsive moiety of the targeted redox-responsive polymer to form a targeted stimuli-responsive polymer-drug conjugate, wherein pH-responsive moiety comprises an acid-labile linkage that is hydrolyzed between pH 5 and pH 7, and the drug complex comprises a hydrophobic drug covalently linked to the pH-responsive moiety; and
   (d) adding the targeted stimuli-responsive polymer-drug conjugate into an aqueous liquid to allow self-assembly into a stimuli-responsive multifunctional nanoparticle, wherein the hydrophobic drug of the stimuli-responsive multifunctional nanoparticle forms a hydrophobic core.

2. The method of claim 1, further comprising the step of adding an imaging agent into the aqueous liquid in step (d) to allow the imaging agent to be incorporated within the hydrophobic core of the stimuli-responsive multifunctional nanoparticle.

3. The method of claim 2, wherein the imaging agent is a near-infrared fluorescent dye.

4. The method of claim 1, wherein in step (a) the hyaluronic acid has a molecular weight of below 20 kDa.

5. The method of claim 1, wherein in step (a) the peptide has 5-20 amino acid residues.

6. The method of claim 1, wherein the peptide is a luteinizing hormone-releasing hormone peptide or an analog thereof.

7. The method of claim 1, wherein redox-responsive moiety is cystamine or an analog thereof.

8. The method of claim 1, wherein the pH-responsive moiety is a cis-aconityl group.

9. The method of claim 1, wherein in step (c) the hydrophobic drug is an anticancer drug.

10. The method of claim 2, wherein in step (d) the targeted stimuli-responsive polymer-drug conjugate and the imaging agent are in a weight ratio of about 10:1 to 15:1.

11. The method of claim 1, wherein the stimuli-responsive multifunctional nanoparticle is at a size of about 150-300 nm.

* * * * *